United States Patent [19]

Rock et al.

[11] Patent Number: 5,767,288

[45] Date of Patent: Jun. 16, 1998

[54] PHOTOLABILE LINKERS AND PROBES

[75] Inventors: Ronald S. Rock; Michael H. B. Stowell, both of Pasadena; Sunney I. Chan, South Pasadena, all of Calif.

[73] Assignee: California Institute of Technology, Pasadena, Calif.

[21] Appl. No.: 583,994

[22] Filed: Jan. 5, 1996

[51] Int. Cl.$^6$ ............... C07D 339/08; C07D 307/78; C07D 271/12; C07C 49/23

[52] U.S. Cl. ............... 549/22; 549/469; 548/126; 568/329

[58] Field of Search ............... 549/22, 469; 548/126; 568/329

[56] References Cited

U.S. PATENT DOCUMENTS

| | | | |
|---|---|---|---|
| 3,702,854 | 11/1972 | Jurd | 549/469 |
| 3,901,908 | 8/1975 | Fitzi et al. | 548/343.5 |
| 4,469,774 | 9/1984 | Lee | 430/270 |
| 5,200,334 | 4/1993 | Dunn et al. | 432/182 |

OTHER PUBLICATIONS

Pirrung, M.C., et al., "Dimethoxybenzoin Carbonates: Photochemically–Removable Alcohol Protecting Groups Suitable for Phosphoramidite–Based DNA Synthesis", *J. Org. Chem.* 60:1116–1117 (1995).

Gurney, A.M., et al., "Light Flash Physiology with Synthetic Photosensitve Compounds", *Physiological Reviews* 67(2):583–617 (1987).

Pillai, V.N.R., "Photoremovable Protecting Groups in Organic Synthesis", *Review*spp. 1–27 (1980).

Cameron, J.F., et al., "New Photolabile Amino Proecting Groups: Photogeneration of Amines from [3',5'-Dimethoxybenzoinyl)oxy]carbonyl Carbamates", *J. Chem. Soc., Chem. Commun.* pp. 923–924 (1995).

Pirrung, M.C., et al., "Photoremovable Protecting Groups for Phosphorylation of Chiral Alcohols. Asymmetric Synthesis of Phosphotriesters of (−)–3',5'–Dimethoxybenzoin" *J. Org. Chem.* 59:3890–3897 (1994).

McCray, J.A., et al., "Properties and Uses of Photoreactive Caged Compounds", *Annu. Rev. Biophys. Chem.* 18:239–270 (1989).

Cummings, R.T., et al., "Photoactivable Fluorohores. 1. Synthesis and Photoactivation of o–Nitrobenzyl–Quenched Fluorescent Carbamates", *Tetrahedron Letters* 29(1):65–68 (1988).

Mendel D., et al., "Construction of a Light–Activated Protein by Unnatural Amino Acid Mutagenesis", *J. Am. Chem. Soc.* 113:2578–2760 (1991).

Corrie, J.E.T., et al., "Synthetic, Mechanistic and Photochemical Studies of Phosphate Esters of Substituted Benzoins", *J. Chem. Soc. Perkin Trans.* 1 pp. 2409–2417 (1992).

Pirrung, M.C., et al., "Photochemical Deprotection of 3'–5'–Dimethoxybenzoin (DMB) Carbamates Derived from Secondary Amines", *Tetrahedron Letters* 36(33):5883–5884 (1995).

Sheehan, J.C., et al., "The Photolysis of Methoxy–Substituted Benzoin Esters. A Photosensitive Protecting Group for Carboxylic Acid", *Journal of the American Chemical Society* 93(26):7222–7228 91971).

Krepski, L.R., et al., "Addition of Grignard Reagents to o–Trimethylsilylated Cyanohydrins: Synthesis of Acyloins", *Angew. Chem. internat. Edit* 4(12):4075 (1965).

*Primary Examiner*—José G. Dees
*Assistant Examiner*—Deborah Lambkin
*Attorney, Agent, or Firm*—Flehr Hohbach Albritton & Herbert LLP

[57] ABSTRACT

The invention relates to dithiane adducts of substituted benzoins and substituted benzoins derived therefrom each of which are useful as protecting groups, photolabile linkers, and fluorescent probes.

13 Claims, 4 Drawing Sheets

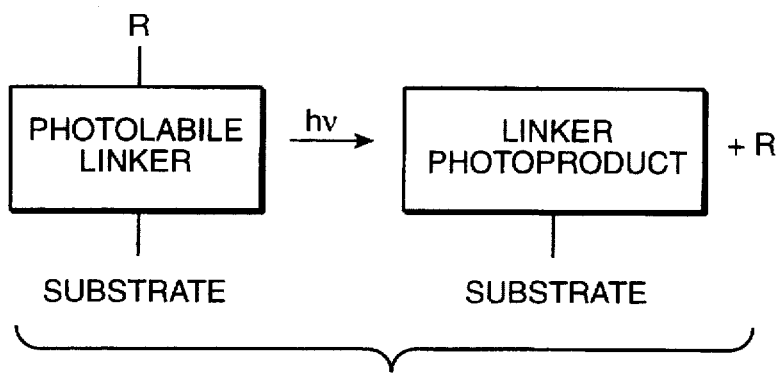
FIG._1
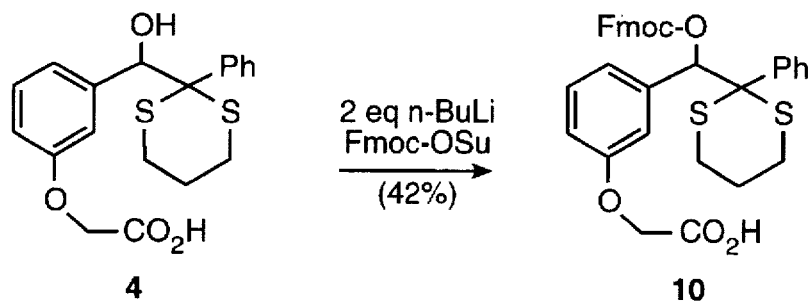
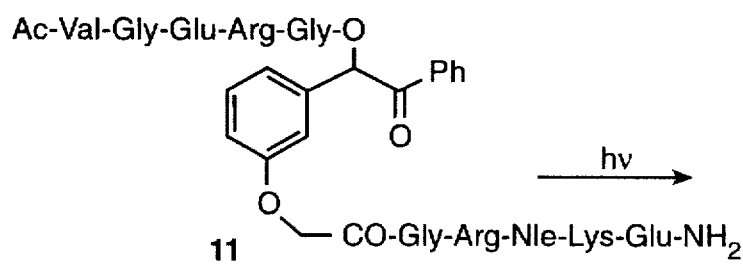
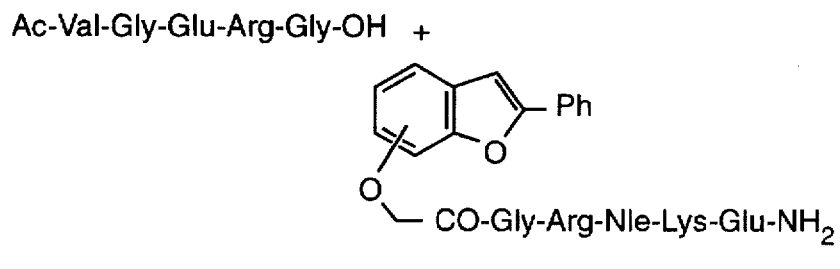
FIG._3

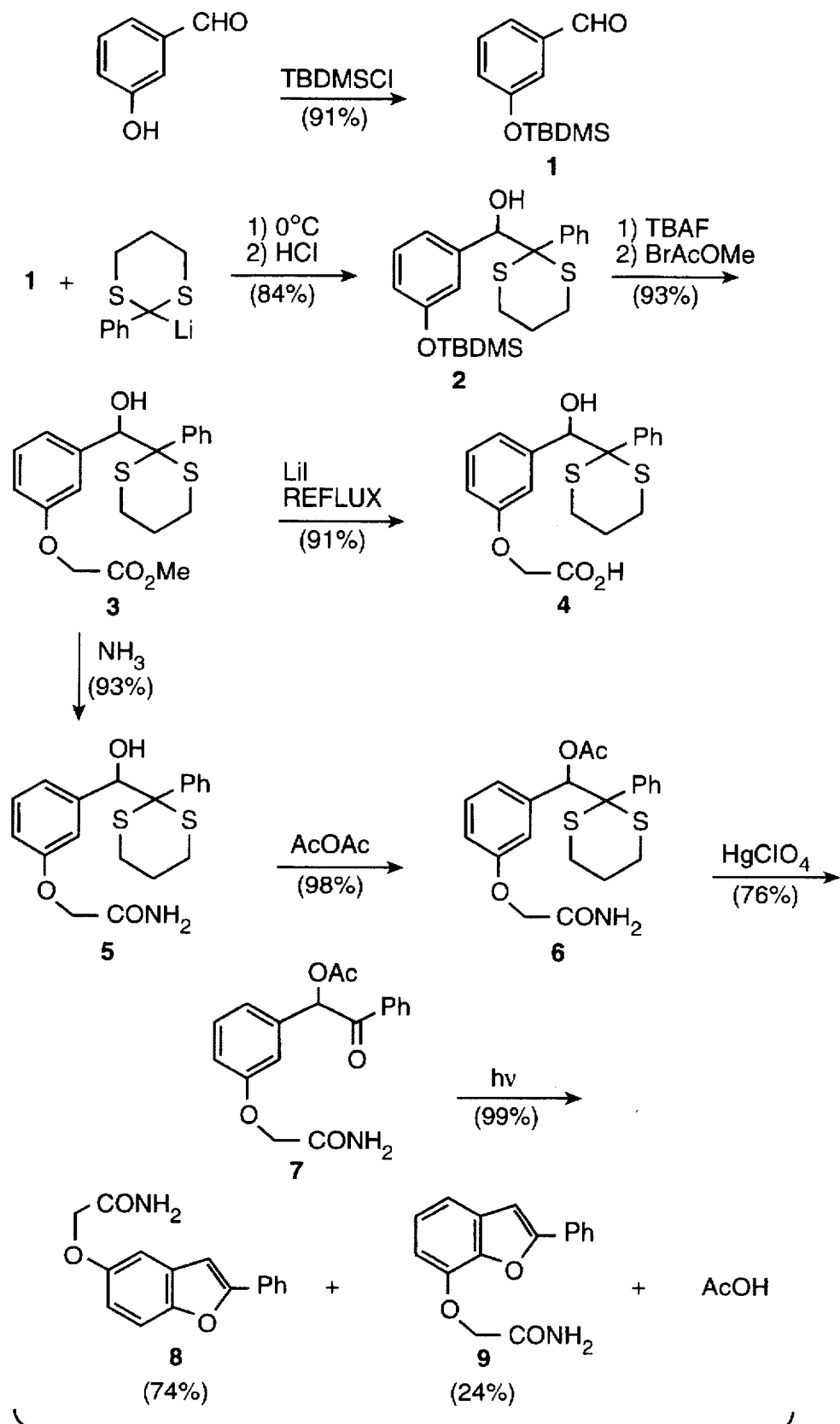
FIG._2

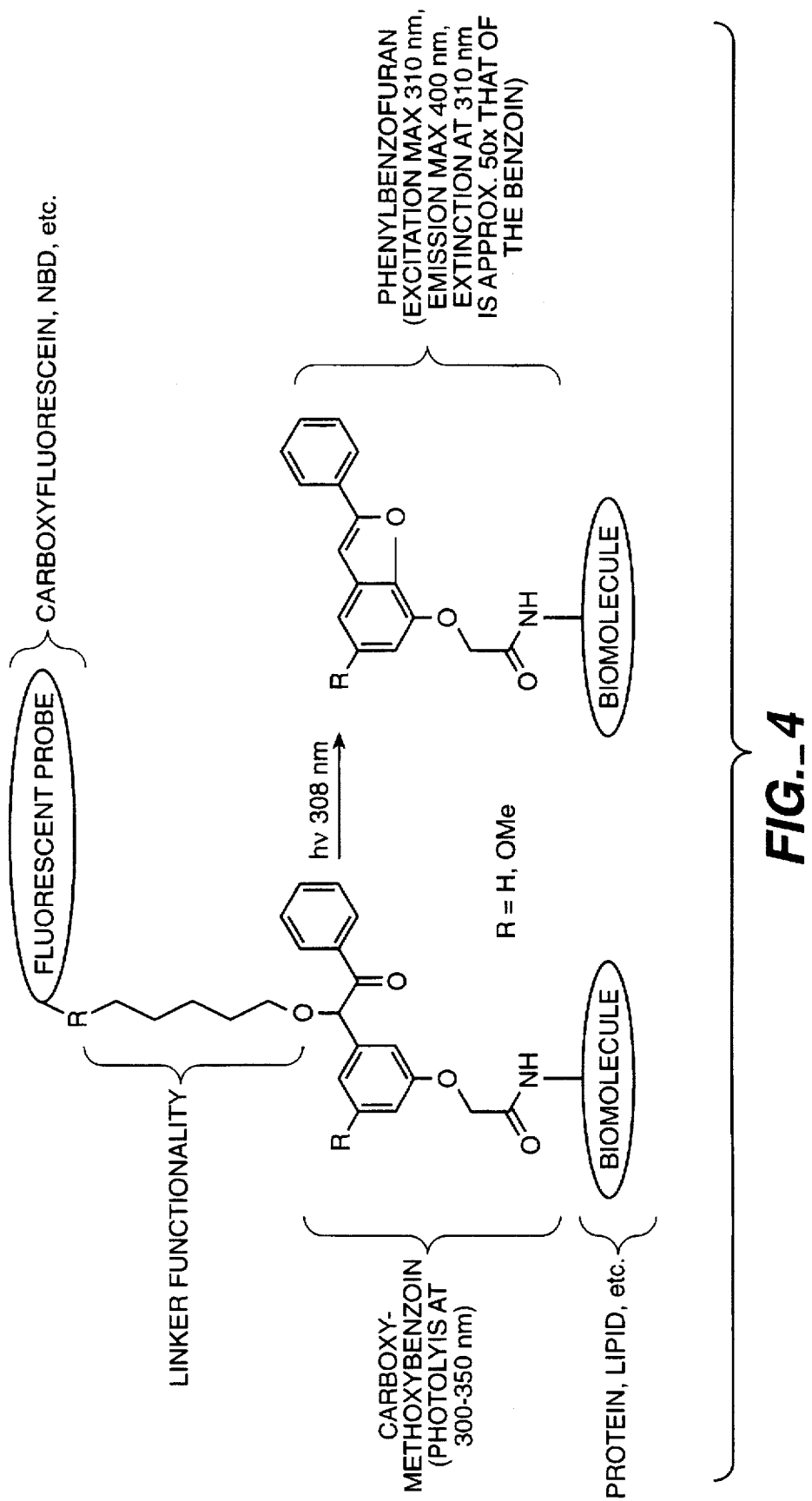
FIG._4

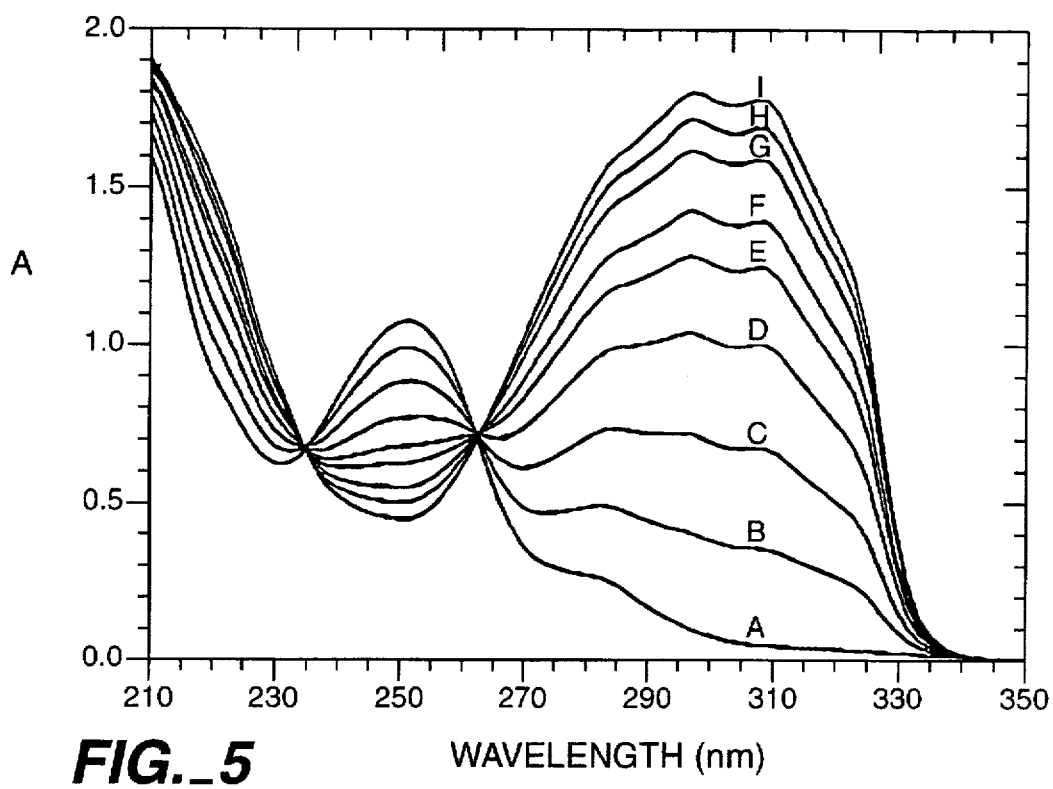
FIG._5
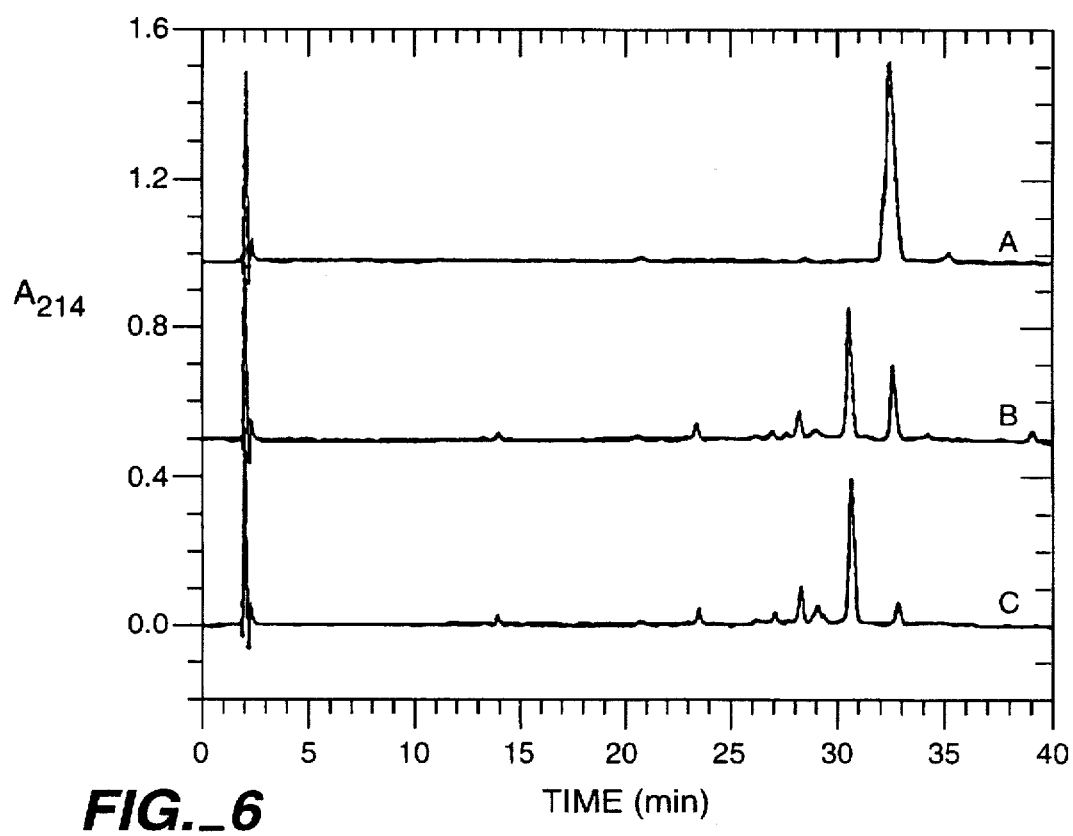
FIG._6

PHOTOLABILE LINKERS AND PROBES

The U.S. Government has certain rights in this invention pursuant to Grant No. GM 22432 awarded by the National Institute of Health.

FIELD OF THE INVENTION

The invention relates to dithiane adducts of substituted benzoins and substituted benzoins derived therefrom each of which are useful as protecting groups, photolabile linkers, and fluorescent probes.

BACKGROUND OF THE INVENTION

The use of protecting groups in organic synthesis has been invaluable in allowing the complete synthesis of numerous complex organic molecules (Greene, T. W. *Protective Groups in Organic Synthesis*, John Wiley and Sons, Inc: New York.1991. A number of protecting groups in organic synthesis have the convenient property that they can be removed photochemically. The synthesis and photocleavage properties of a series of substituted nitrobenzyl protecting groups have been described (Patchornik, A.; Amit, B.; Woodward, R. B. *J. Am. Chem. Soc.* 1970, 92, 6333). Such protecting groups have played important roles in the synthesis of complex, polyfunctional organic molecules.

These materials have been used in such diverse fields as semiconductor lithography (Sabomgi, G. J. *Chemical Triggering*, Plenum: 1987) and the study of rapid enzymatic processes (Gurney, A. M.; Lester, H. A. *Physiol. Rev.* 1987, 67, 583; McCray, J. A.; Trentham, D. R. *Annu. Rev. Biophys. Chem.* 1989, 18, 239). For example, they have been used to "cage" compounds by protection of an essential functional group, so that a chemical reaction may be initiated by a pulse of light. In this manner, mixing difficulties can be circumvented in kinetic measurements (Corrie et al., *J. Chem. Soc. Perkin. Trans* 1:2409 (1992); Pirrung et al., *J. Org. Chem* 59:3890 (1994)). Applications of this method include the photolysis of caged ATP for studies of muscle fiber contraction, where diffusion of ATP into the muscle fiber is slow (Harrison, L. T.; Harrison, S. *Compendium of Organic Synthetic Methods*, Vol II; John Wiley and Sons, Inc: New York, 1974; pp 302–307. Hegedus, L. S.; Wade, Jr., L. G.; *Compendium of Organic Synthetic Methods*, Vol III John Wiley and Sons, Inc: New York, 1977; pp 366–369. Wade, Jr., L. G.; *Compendium of Organic Synthetic Methods*, Vol II; John Wiley and Sons, Inc: New York, 1980; pp 375–379); of caged fluorescent probes that only emit light after photolysis (Krepski et al., Tetrahedron Letters 24, 38 4075 (1983); and even of caged enzymes by incorporating photolabile groups on essential side chains (Corey et al., D. Angew. Chem. Int. Ed. Engl. 4:1075 (1965)).

Another application for photoinitiated molecules is within the area of intracellular probes. Cellular traffic and the effects of cellular stimuli on cellular traffic are areas of active research. The goal is to understand how extra-and intra-cellular signals affect the trafficking and accumulation of important biomolecules. The most common method of studying cellular traffic is through the use of fluorescent probes which can be covalently linked to biomolecules and thus allow for easy identification and quantitation (for numerous examples see the Molecular Probes catalog). These cellular trafficking studies are hampered, in part, by the inability to generate a specific fluorescent signal at a particular site in a cell. Consequently if a fluorescent-labeled biomolecule is introduced into a cell, it distributes throughout its targeted organelles and fluorescence measurements can be performed to determine the location and quantity of such biomolecules. If the cell environment is then perturbed, only gross changes in the labeled biomolecule concentration and location can be detected. As a result, it is possible to observe a large increase in fluorescence in one organelle and a decrease in another in such an experiment, but information about the pathway of transport, where small populations of the biomolecule may be present, is lost. This is due to the fact that only intensity differences at the emission wavelength of the fluorophore can be observed using such techniques. For the same reason, it is impossible to study steady-state transport processes by these standard fluorescence techniques.

Several photolabile moieties are currently available. The photolysis properties of compounds such as nitrobenzyl esters (McCray et al., supra), phenacyl esters (Baldwin et al., Tetrahedron 46:6879 (1990)) and benzoin esters (Corrie, supra; Pirrung 1994, supra) of carboxylates and phosphates have been well studied. Such photolabile compounds have only a single functional group for attachment, rendering them unsuitable for linkage.

One class of protecting groups that have seen less use are the substituted benzoins initially reported by Sheehan et al., J. Am. Chem. Soc. 93:7222 (1971). Of particular interest are the substituted alkoxybenzoins which have quite remarkable photocleavage properties. An example is the 3',5'-dimethoxybenzoin (3',5'-DMB) protecting group which undergoes a photoinitiated cyclization and cleavage as shown in Equation 1, with a rate constant estimated to be greater than $10^{10} sec^{-1}$ and a quantum efficiency of 0.64, where $R_1$ is acetyl.

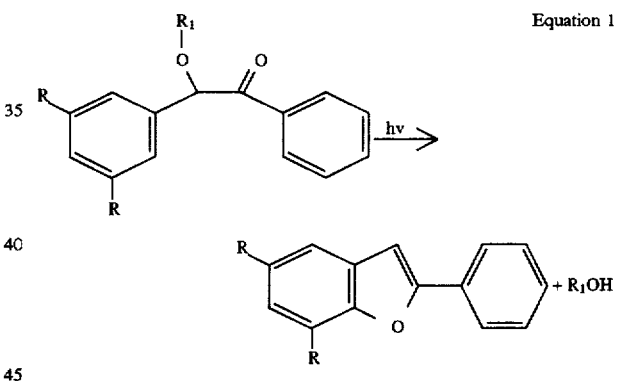

Equation 1

Such a protecting group is of considerable interest, not only in synthesis, but also for the study of rapid enzyme kinetics and several recent papers have described the use of the 3',5'-DMB as a protecting group in oligonucleotide synthesis (Pirrung, 1995, supra) and for 'caged' substrates. Advantages of the 3',5'-DMB versus substituted nitrobenzyl protecting groups are the rapid release rate, high quantum yield, and the easily detectable, nonreactive, benzofuran photoproduct.

While the 3',5'-DMB protecting group has many advantages, there are two distinct disadvantages to using such a protecting group. First, while considerable effort has gone into the synthesis of acyloins, many of these methods have proven to be inefficient for a number of targeted acyloins, in particular 3',5'-DMB. Secondly, due to the remarkable photocleavage properties of the 3',5'-DMB protecting group, photolysis occurs in standard laboratory light and samples must be kept in complete darkness, thus making subsequent synthetic transformations cumbersome.

U.S. Pat. No. 4,469,774 describes the synthesis of photosensitive benzoin ester polymers for use in lithographic processes.

Thus, there is a need for methods to synthesize complex protected molecules that are capable of remaining photochemically stable until a later time.

SUMMARY OF THE INVENTION

In accordance with the objects outlined above, the present invention provides compounds having the formula comprising

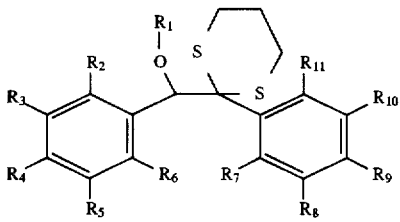

In this embodiment, $R_1$ is hydrogen, carboxy, substituted carbonyl, a phosphorus containing group, a sulfur containing group, a fluorescent label or a biomolecule. $R_2$ to $R_{11}$ are each hydrogen, alkyl, aryl, alkoxy or substituted alkoxy. At least one of $R_2$ or $R_6$ is hydrogen, and at least one of $R_2$, $R_3$, $R_4$, $R_5$ or R6 is hydroxy or substituted alkoxy.

The invention further provides compounds having the formula comprising:

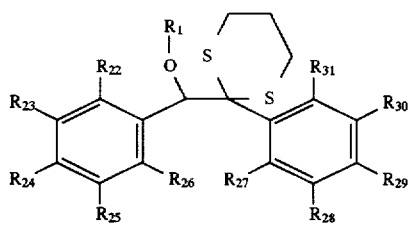

In this embodiment, $R_1$ is hydrogen, carboxy, substituted carbonyl, phosphorus-containing moiety, a sulfur containing group, a fluorescent label or a biomolecule. $R_{22}$ through $R_{31}$ are each hydrogen, alkyl, aryl, alkoxy, substituted alkoxy, or a biomolecule. In this embodiment, at least one of $R_{22}$ or $R_{26}$ is hydrogen, at least one of $R_{22}$, $R_{23}$, $R_{24}$, $R_{25}$ or $R_{26}$ is alkoxyl or substituted alkoxy; and at least one of $R_{22}$, $R_{23}$, $R_{24}$, $R_{25}$ or $R_{26}$ is a biomolecule.

Also provided are the corresponding substituted benzoins:

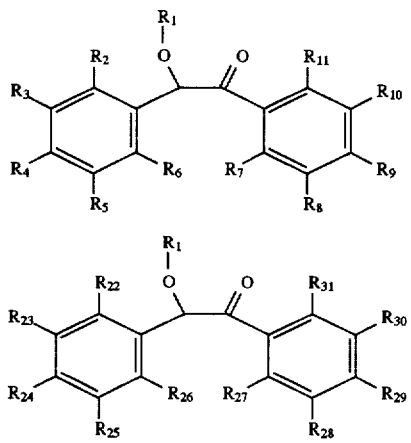

Also provided are the furan photolysis products obtained by the photolysis of a substituted benzoin of the invention.

Further provided are methods for forming the dithiane-benzoin adducts.

BRIEF DESCRIPTION OF THE DRAWINGS

FIG. 1 schematically depicts the linkers of the invention.

FIG. 2 schematically depicts the synthesis of the compounds of the invention.

FIG. 3 depicts the incorporation of a linker of the invention into a peptide.

FIG. 4 schematically depicts a novel fluorescent probe of the invention.

FIG. 5 shows the steady-state photolysis of benzoin acetate 7. A 47.7 µM solution of 7 in 1:1 methanol/Tric-HCl (0.05 M, pH 7.40) was irradiated with an Oriel 66011 Hg vapor lamp; irradiation time in seconds: A,0; B, 2; C, 5; D, 10; E, 15; F, 20; G, 30; H, 40; I,90.

FIG. 6 depicts the steady state photolysis of peptide 11, as monitored by reverse-phase (C1 8) HPLC. The two C-terminal phenylbenzofuran containing peptides elute at 28.5 and 31.0 min, while the N-terminal peptide elutes in the void volume. Some photodegradation of the benzofuran is also apparent at retention times below 30 min. Gradient: 0–35% acetonitrile in water, 0.1% TFA, detection: 214 nm. Irradiation time in minutes: A, 0; B, 5; C, 10.

DETAILED DESCRIPTION OF THE INVENTION

The present invention provides novel photolabile compounds and precursors of such photolabile compounds, and the products formed after photolysis. The photolabile and precursor compounds have a wide variety of utilities including protecting groups, photolabile linkers and fluorescent probes. While benzoin photolabile protecting groups are known, photolysis frequently occurs in standard laboratory light, making subsequent synthetic transformations cumbersome. However, the addition of a dithiane adduct as described herein renders the precursor photochemically stable until the conversion of the dithiane to a ketone is accomplished. Exposure to light then results in photolysis. Thus, the invention provides for stable photolabile precursor protecting groups for use in the synthesis of a wide variety of compounds.

The invention also provides photolabile and photolabile precursor compounds that serve as linkers; that is, they have two functional groups for attachment of other compounds. Thus, the present invention provides photolabile linkers and photolabile precursor linkers that can hold two moieties together until at least one of them is released by exposure to light. Since the photolysis reaction is extremely rapid and avoids the problems associated with mixing, these novel linkers find use in "caging" reactions, solid phase synthetic reactions, and protein folding studies.

Furthermore, these linkers may be used to construct novel fluorescent probes that can rapidly change emission colors in response to a photolysis pulse.

Thus for example, probes are constructed that comprise a biomolecule of interest linked to one fluorescent probe. Upon photolysis, a new fluorescent signal at a different wavelength is generated, thus allowing the tracking of the newly generated signal against the background of the original signal.

The dithiane adducts depicted in Formulas 1 and 2, below, may be either intermediate compounds, i.e. containing functional groups that will allow the attachment of desired molecules, or compounds containing the desired molecules.

Thus, for example, the $R_1$ group and any one of $R_2$ to $R_6$ (or the corresponding groups of Formula 2) may contain functionally active groups including hydroxy, amino or carboxy groups that can be used to add biomolecules such as enzyme substrates, or other molecules of interest such as fluorescent labels. Alternatively, either $R_1$ or $R_2$ to R6 may be a chemically reactive group and the other reactive group may have been used to add the desired moiety such as an enzyme substrate, such that the compound already comprises one attached biomolecule. Similarly, both the $R_1$ and $R_2$ to $R_6$ may comprise desired moieties such as fluorescent labels and/or biomolecules.

Furthermore, the compounds of the invention comprise the dithiane adduct (i.e., a precursor of a photolabile substituted benzoin) as depicted in Formulas I and 2, or the dithiane may be removed to form the photolabile substituted benzoin, as is depicted in Formulas 3 and 4.

In one embodiment, the present invention provides novel photolabile precursor compounds as generally depicted in Formula 1:

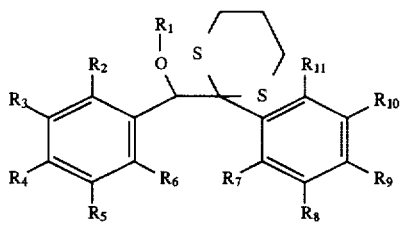

Formula 1

In this embodiment, $R_1$ is hydrogen, carboxy, substituted carbonyl, a phosphorus-containing moiety, a sulfur-containing moiety, a fluorescent label or a biomolecule. $R_2$, $R_3$, $R_4$, $R_5$, $R_6$, $R_7$, $R_8$, $R_9$, $R_{10}$, and $R_{11}$, are each hydrogen, alkyl, aryl, alkoxy, substituted alkoxy, or halide. At least one of $R_2$ or $R_6$ is hydrogen. At least one of $R_2$, $R_3$, $R_4$, $R_5$ and R6 is hydroxy or substituted alkoxy.

By "carboxy" herein is meant a —COOH or —COOR$_{12}$ group, such that the —ORI group is a carbonate group. $R_{12}$ is as defined below.

By "substituted carbonyl" herein is meant a —COR$_{12}$ group, where $R_{12}$ may be hydrogen, alkyl, aryl, alkyl amine, amine, secondary amine, alkoxy, a biomolecule or a fluoroscent label. Thus, the ORI may be a carbamate of the formula —OCONRR'. When the substituted carbonyl comprises the $R_1$ group, and $R_{12}$ is an amine group, secondary amines are preferred.

By "alkyl" or "alkyl group" or grammatical equivalents herein is meant a straight or branched chain alkyl group, with straight chain alkyl groups being preferred. If branched, it may be branched at one or more positions, and unless specified, at any position. Also included within the definition of an alkyl group are cycloalkyl groups such as C5 and C6 rings. In some cases, two R groups may be part of a ring structure, that is, they may be linked to form a cyclic structure, including heterocyclic structures. For example, as described in Pillai, Synthesis, January 1980, pp 1–26, incorporated herein by reference, $R_3$ and $R_4$ and/or $R_9$ and $R_{10}$ may be joined to form a methylene dioxy five membered ring; in addition, $R_2$ and $R_3$, and/or $R_7$ and $R_8$ may also be similarly joined (or the corresponding positions in Formula 2). In some cases, the R groups may form an aryl group; for example, as described in U.S. Pat. No. 4,469,774, R9 and $R_{10}$ may form a benzyl group, such that a naphthyl group is formed.

The alkyl group may range from about 1 to 100 carbon atoms (C1–C100), with a preferred embodiment utilizing from about 1 to about 20 carbon atoms (C1–C20), with about C1 through about C5 being preferred. However, in some embodiments, the alkyl group may be larger, particularly if it is a straight chain alkyl. Particularly preferred is methyl in the $R_2$ to $R_{11}$ and $R_{22}$ to $R_{31}$ positions.

By "aryl" or "aryl group" herein is meant aromatic rings including phenyl, benzyl, and naphthyl, heterocyclic aromatic rings such as pyridine, furan, thiophene, pyrrole, indole and purine, and heterocyclic rings with nitrogen, oxygen, sulfur or phosphorus.

The alkyl and aryl groups may be substituted, for example, a phenyl group may be a substituted phenyl group. Suitable substitution groups include, but are not limited to, alkyl and aryl groups, halogens such as chlorine, bromine and fluorine, amines, carboxylic acids, and nitro groups.

By the term "amine" herein is meant an —NR$_{13}$R$_{14}$ group. In this embodiment, $R_{13}$ and $R_{14}$ may be the same or different, and may be hydrogen, alkyl or aryl. A preferred —NR$_{13}$R$_{14}$ group is —NH$_2$. A secondary amine is —NR$_{13}$R$_{14}$ when neither $R_{13}$ nor $R_{14}$ is hydrogen.

By "hydroxy" herein is meant a —OH group.

By "alkoxy" herein is meant an —OR$_{15}$ group, where $R_{15}$ is an alkyl group as depicted above. Included within the definition of alkoxy is methoxy (—OCH$_3$).

By "substituted alkoxy" herein is meant a —OXC(R$_{16}$)(R$_{17}$)(R$_{18}$) group, wherein X is either not present (i.e. substituted methoxy) or a straight or branched chain alkyl group. In a preferred embodiment, X is a straight chain alkyl group, such that the substituted alkoxy group has the formula —O(CH$_2$)$_n$C(R$_{16}$)(R$_{17}$)(R$_{18}$), wherein n is zero (substituted methoxy, which is preferred) or greater, preferably from 1 to 100, with I to 20 being especially preferred. $R_{16}$, $R_{17}$ and $R_{18}$ are selected from the group consisting of amino, carboxy, phosphorus-containing moieties, sulfur-containing moieties, protecting groups such as silyl groups and others known in the art, biomolecules, or fluorescent labels. In a preferred embodiment, $R_{16}$ and $R_{17}$ are hydrogen, such that there is a single substitution group.

By "phosphorus containing moiety" herein is meant a functional group containing at least one phosphorus atom. In a preferred embodiment, the phorphorus containing moiety is chemically or functionally active, such that further groups may be attached to the compound using the phosphate. In a preferred embodiment, the phosphorus-containing moiety is a phosphate (—OPO(OH)$_2$ group), pyrophosphates, or a substituted phosphate group of the formula —OPO(OR$_{19}$)(OR$_{20}$). When $R_1$ is a phosphorus containing moiety, it should be understood that the first oxygen attached to the phosphorus atom is the oxygen depicted in the Formulas as attached to $R_1$. In all embodiments, the formation of peroxide groups (—O—O—) is not preferred. In this embodiment, $R_{19}$ and $R_{20}$ include, but are not limited to, hydrogen, alkyl, or aryl. In a preferred embodiment, one of $R_{19}$ and $R_{20}$ is hydrogen. Also included within the definition of phosphorus containing moieties are phosphines (—R$_3$P), and phosphonates (—RPO(OR$_{19}$)(OR$_{20}$)).

By "sulfur containing moiety" herein is meant a functional group containing at least one sulfur atom. As for the phosphates, the sulfur containing moiety is preferably chemically or functionally active, such that further groups such as 15 biomolecules may be attached using the sulfur atom. Thus thiols (—RSH), sulfides (RSR'), sulfoxides (—SO—), sulfones (—SO$_2$—), sulfates (—OSO$_2$O—), and sulfonic acids (—RSO$_2$OH) are all included within the definition of sulfur containing moieties. It should be noted that when the sulfur containing moiety is at the $R_1$ position and is a sulfate, one of the oxygens of the sulfate is the oxygen depicted in the Formulas as attached to $R_1$; that is, a peroxide is not formed. By "halide" herein is meant a halide atom. Preferred halides include chlorine, fluorine, bromine and iodine, with chlorine and fluorine being particularly preferred, and chlorine being most preferred.

By "fluorescent label" or grammatical equivalents herein is meant any one of the large number of known molecules that fluoresces in response to activation with light. In a preferred embodiment, the emission wavelength of the fluorescent label is widely separated from the emission wavelength of the photolysis product (i.e. phenylbenzofuran) to allow for differentiation of the two. Preferably the fluorescent label will fluoresce at wavelengths that do not result in photolysis, such that the compound containing the fluorescent label can be followed prior to photolysis. Photolysis of the substituted benzoin compounds of the invention generally occurs between 300 to 360 nm. Phenylbenzofuran has an excitation maximum at 310 nm and an emission maximum at 400 nm. Accordingly, preferred fluorescent labels have emission maximum above 400 nm. Preferred fluorescent labels include, but are not limited to, carboxyfluorescein, 6-(N-(7-nitrobenz-2-oxa-1,3-diazol-4-yl)amino hexanoic acid (NBD), carboxytetramethylrhodamine, Texas Red, R-phycoerythrin, amino methyl coumarin, C-SNARF-1, Lucifer yellow, dansyl, ANS, Cascade blue, or any of the BODIPY series from Molecular Probes (see 1989–1991 Molecular Probes catalog).

As will be appreciated in the art, a large number of possible "biomolecules" may be attached to the linkers of the present invention, for a wide variety of purposes. "Biomolecule" includes, but is not limited to, polypeptides, carbohydrates, lipids, nucleic acids, hormones, receptor ligands, antibodies, enzyme substrates and inhibitors, and antigens.

By the term "polypeptide" herein is meant a compound ranging from about I to about 500 amino acid residues covalently linked by peptide bonds, and thus includes peptides, polypeptides, and proteins. Preferred embodiments utilize polypeptides from about 1 to about 100 amino acids, with about 1 to about 50 being the most preferred. In some instances, for example when the polypeptide is an enzyme substrate or inhibitor, the polypeptide is preferably in the 1 to 10 amino acid range. Preferably, the amino acids are naturally occurring amino acids in the L-configuration, although amino acid analogs are also useful, as outlined below. Under certain circumstances, the polypeptide may be only a single amino acid residue. Additionally, in some embodiments, the polypeptide may be larger, and thus fall under the more traditional definition of a protein. In one embodiment, the polypeptide is glycosylated.

The polypeptide may be an enzyme, a substrate, a ligand for a receptor, growth hormones, cytokines, cofactors, antibodies, and antigens.

Also included within the definition of polypeptide are peptidomimetic structures or amino acid analogs. Thus, for example, non-naturally occurring side chains or linkages may be used, for example to prevent or retard in vivo degradations. Alternatively, the amino acid side chains may be in the (R) or D-configuration. Additionally, the amino acids, normally linked via a peptide bond or linkage, i.e. a peptidic carbamoyl group, i.e. —CONH—, may be linked via peptidomimetic bonds. These peptidomimetic bonds include $CH_2$—NH—,CO—CH, azapeptide and retroinversion bonds.

As used herein, "nucleic acid" may refer to either DNA or RNA, or molecules which contain both deoxy- and ribo-nucleotides. Generally, the nucleic acid is an oligonucleotide, ranging from about 3 nucleotides to about 50 nucleotides, with from about 12 to about 36 being particularly preferred, and at least 21 nucleotides being especially preferred. When the nucleic acid is used solely to confer solubility, the nucleic acid may be smaller, and in some embodiments may be a single nucleotide. The nucleotides may be naturally occurring nucleotides, or synthetic nucleotides, and may be any combination of natural and synthetic nucleotides, although uracil, adenine, thymine, cytosine, guanine, and inosine are preferred. As is more fully described below, the nucleic acids include genomic DNA, cDNA and oligonucleotides including sense and anti-sense nucleic acids. The nucleic acid may be double stranded, single stranded, or contain portions of both double stranded or single stranded sequence.

A nucleic acid will generally contain phosphodiester bonds, although in some cases, as outlined below, a nucleic acid may have an analogous backbone, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate, phosphorodithioate, O-methylphosphoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); Nielsen, Nature, 365:566 (1993)). These modifications of the ribose phosphate backbone may be done to facilitate the addition of the compounds of the invention, as outlined below, or to increase the stability and half-life of such molecules in physiological environments.

By "carbohydrate" herein is meant a compound with the general formula $C_x(H_2O)_y$. Monosaccharides, disaccharides, and oligo- or polysaccharides are all included within the definition and comprise polymers of various sugar molecules linked via glycosidic linkages. Particularly preferred carbohydrates are those that comprise all or part of the carbohydrate component of glycosylated proteins, including monomers and oligomers of galactose, mannose, fucose, galactosamine, (particularly N-acetylglucosamine), glucosamine, glucose and sialic acid, and in particular the glycosylation component that allows binding to certain receptors such as cell surface receptors. Other carbohydrates comprise monomers and polymers of glucose, ribose, lactose, raffinose, fructose, and other biologically significant carbohydrates.

"Lipid" as used herein includes fats, fatty oils, waxes, phospholipids, glycolipids, terpenes, fatty acids, and glycerides, particularly the triglycerides. Also included within the definition of lipids are the eicosanoids, steroids and sterols, some of which are also hormones, such as prostaglandins, opiates, and cholesterol. Hormones include both steroid hormones and proteinaceous hormones, including, but not limited to, epinephrine, thyroxine, oxytocin, insulin, thyroid-stimulating hormone, calcitonin, chorionic gonadotropin, cortictropin, follicle-stimulating hormone, glucagon, leuteinizing hormone, lipotropin, melanocyte-stimutating hormone, norepinephrine, parathyroid hormone, vasopressin, enkephalins, seratonin, estradiol, progesterone, testosterone, cortisone, and glucocorticoids. Receptor ligands include ligands that bind to receptors such as cell surface receptors, which include hormones, lipids, proteins, glycoproteins, signal transducers, growth factors, cytokines, and others.

As will be generally understood in the art, the actual composition of the biomolecule may be quite broad, and will vary depending on the use of the linker. All that is required is that the biomolecule either contains or can be made to contain a functional group for attachment as an R group.

In one embodiment, the linkage between the complex and the biomolecule is direct. For example, chemically reactive groups of the biomolecule may be used for attachment to the photolabile linkers of the present invention. Thus, as is more fully described below, for example the amino acid side chains of a polypeptide may be used for attachment. Alternatively, when one of the R groups is a biomolecule such as a polypeptide, nucleic acid, carbohydrate, etc., there may be a linker between the biomolecule and the core dithiane or benzoin molecules of the invention. For example, homo-or hetero-bifunctional linkers as are well known in the art (see 1994 Pierce Chemical Company catalog, 10 technical section on cross-linkers, pages 155–200, incorporated herein by reference) may be used to link the biomolecule to the compounds of the invention.

The compounds of the invention have at least one hydrogen as either $R_2$ or $R_6$ in Formula 1 (or $R_{22}$ or $R_{26}$ in Formula 2). This is required due to the photolysis mechanism depicted in Equation 1, wherein a furan ring is formed by attack at either the $R_2$ or $R_6$ position. Accordingly, at least one of these positions must be hydrogen; i.e. it must not contain a substitution group. In a preferred embodiment, both of $R_2$ and $R_6$ in Formula 1 and $R_{22}$ and $R_{26}$ in Formula 2 are hydrogen.

At least one of $R_2$, $R_3$, $R_4$, $R_5$, or $R_6$ of the compounds of the invention as depicted in Formula 1 are hydroxy or substituted alkoxy. Similarly, at least one of $R_{22}$ to $R_{26}$ is alkoxy or substituted alkoxy. As has been reported for the photolabile benzoins, the presence of methoxy groups in the two meta positions improves the yield and rate of the photolysis reaction. Thus, in a preferred embodiment, at least one of the $R_2$, $R_3$, $R_4$, $R_5$ or R6 groups has an oxygen atom attached to the ring. Preferably the oxygen atom is attached at either or both of the meta positions ($R_3$ and $R_5$). In a preferred embodiment, at least $R_5$ has an oxygen atom in the form of a hydroxy or substituted alkoxy group. Alternatively, the oxygen atom is attached at the para position ($R_4$ or $R_{24}$), or ortho positions ($R_2$ and $R_6$, or $R_{22}$ and $R_{26}$), although as outlined above, at least one of $R_2$ or $R_6$ (or $R_{22}$ and $R_{26}$) is hydrogen.

The hydroxy group and the substituted alkoxy group facilitate the addition of biomolecules and/or fluorescent labels. Alternatively, the alkoxy group may be substituted, for example with a biomolecule and/or fluorescent label.

In a preferred embodiment, the $R_7$, $R_8$, $R_9$, $R_{10}$ and $R_{11}$, groups are all hydrogen. In an additional embodiment, the $R_7$, $R_8$, $R_9$, $R_{10}$ and $R_{11}$ groups can each be alkyl, aryl, alkoxy or substituted alkoxy, or may be a group used to increase the solubility of the compound, as is more fully described below.

In the compound depicted generally in Formula 1, the hydroxy or substituted alkoxy group may donate the oxygen atom directly attached to the ring putatively required for photolysis, as well as supply the chemically reactive group for the attachment of important moieties. There may be additional alkoxy groups on the ring as well. In the compound depicted in Formula 2, the biomolecule or moiety of interest is attached to a ring of the benzoin, with or without a linker, and the oxygen atom is provided by an alkoxy or substituted 2 0 alkoxy group. Thus, in this embodiment, methoxy groups can be attached to the ring.

In a preferred embodiment, the compounds of the invention have the formula depicted in Formula 2:

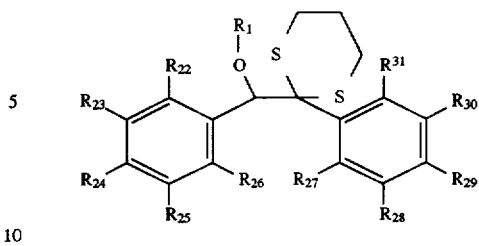

Formula 2

In this embodiment, $R_1$ is hydrogen, carboxy, substituted carbonyl, phosphorus-containing moiety, a sulfur-containing moiety, a fluorescent label or a biomolecule. $R_{22}$ thorugh $R_{26}$ are each hydrogen, alkyl, aryl, alkoxy, substituted alkoxy, or a biomolecule. In one embodiment, at least one of $R_{22}$, $R_{23}$, $R_{24}$, $R_{25}$, or $R_{26}$ is a biomolecule. When none of the R groups of Formula 2 is a biomolecule or a label, it is preferred that $R_{23}$ and $R_{25}$ are not both methoxy. Similarly, when there is no biomolecule or label, it is preferred that $R_{23}$ and $R_{24}$, and $R_{29}$ and $R_{30}$, do not form either methylene dioxy five membered rings nor benzyl rings (to form a naphthyl) with the carbons of the ring.

In one embodiment, at least one of the $R_2$ to $R_{11}$ groups of Formula 1, or the $R_{22}$ to $R_{31}$ groups of Formula 2, are used to increase the solubility of the substituted benzoin or dithiane compound. Since the core structure is hydrophobic, the addition of one or more R groups may increase the solubility of the compound in aqueous solution. By "soluble in aqueous solution" herein is meant that the substituted bezoin or dithiane compound has appreciable solubility in aqueous solution and other physiological buffers and solutions. Solubility may be measured in a variety of ways. In one embodiment, solubility is measured using the United States Pharmacopeia solubility classifications, with the compound being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute). Alternatively, the R groups will allow the formation of greater than 10 mM, preferably greater than 50 mM, and more preferably greater than 100 mM solutions of the compound in aqueous solution. Testing whether a particular compound is soluble in aqueous solution is routine, as will be appreciated by those in the art.

In a preferred embodiment, one R group is used to confer solubility. In alternate embodiments, two or more R groups are used to confer solubility. Suitable solubility -conferring moieties include, but arc not limited to, any number of hydrophilic groups such as biomolecules and labels known to be soluble, carboxylate moieties, (—COOH and —COOR), amine groups, esters, hydroxy groups, alkoxy groups and substituted alkoxy groups, substituted alkyl or aryl groups, when the substitution group is hydrophilic, nitro groups, etc.

In addition to the dithiane-benzoin adducts (the photolabile precursor compounds), the present invention provides the corresponding photolabile benzoin compounds, as depicted below in Formulas 3 and 4:

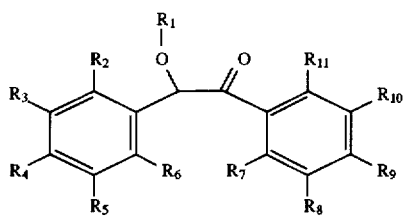

Formula 3

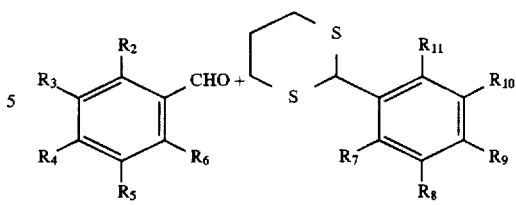

Formula 7

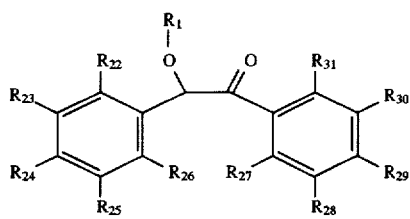

Formula 4

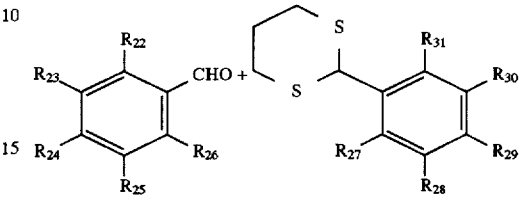

Formula 8

Formula 3 is the corresponding substituted benzoin of the dithiane of Formula 1. Formula 4 is the corresponding substituted benzoin of the dithiane of Formula 2.

The compounds depicted in Formulas 3 and 4 are generally made by removing the dithiane adduct to form the ketone. This is accomplished as is generally known in the art, using mercuric perchlorate or bis(trifluoroacetoxy)-iodobenzene; see for example Greene et al., *Protective groups in Organic Synthesis*, John Wiley and Sons, New York, 1991, pp203–205, hereby incorporated by reference. In this manner, the dithiane adduct serves as a protecting group of the photolabile benzoin, during subsequent manipulations or until photolysis is desired. At the appropriate time, the dithiane adduct is removed, and then photolysis is initiated as needed.

The furan products (Formulas 5 and 6) are formed from the substituted benzoins after exposure to light.

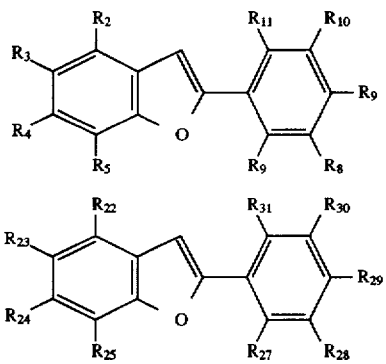

Formula 5

Formula 6

Formulas 5 and 6 depict the furan formed by attack at the R6 or $R_{26}$ position, which were necessarily hydrogen; as will be appreciated by those in the art, the furan may also form at the $R_2$ or $R_{22}$ position.

The dithiane-benzoin adducts of Formulas 1 and 2, and the substituted benzoin compounds of Formulas 3 and 4 are generally synthesized using the scheme depicted in FIG. 2. Generally, this comprises contacting the reactants depicted below in Formula 7 (for the formation of Formula 1 compounds) and Formula 8 (for the formation of Formula 2 compounds):

This is done under conditions that allow the formation of the dithiane-benzoin adducts of the invention.

Generally, the hydroxy group of hydroxybenzaldehyde is protected, using a known protecting group such as a tert-butyldimethylsiloxy group. A dithiane adduct is added, using the Corey-Seebach dithiane addition, to form a dithiane-benzoin compound, compound 2 in FIG. 2. The hydroxyl protecting group is removed, and a chemically active group is added. For example, as shown in FIG. 2, a substituted alkoxy can be added. The substituted alkoxy can be altered to include a chemically reactive group such as a carboxy group (compound 4), or a carbamate (compound 5) at one of the $R_2$ through $R_6$ positions. In a similar manner an amino group, a phosphorus-containing moiety, a sulfur-containing moiety, a substituted carbonyl, a biomolecule or a label or others may be added to the benzyl ring, as is known in the art.

The dithiane-benzoin adducts and benzoins of Formulas 2 and 4 are made as outlined above. When a chemically reactive group is attached directly to the benzyl or benzoyl ring, this may be accomplished by starting with the chemically reactive group attached to the benzaldehyde (for benzyl ring substitutions) or to the dithiane reactant. These are either commercially available or synthesized as is known in the art.

When a biomolecule is to be added to the benzyl or benzoyl ring, or at the $R_1$ position, it may be done in a variety of ways depending on the biomolecule. Generally, when a biomolecule or label is to be attached to the core compound, it is done in two stages. First, the core compound is made containing two chemically active groups; one at the $R_1$ position, and one at one of the other R groups. For example, the core compound is made with amines, carboxy groups, phosphate groups, or sulfhydryl groups, for example. Next, the biomolecule or label is made, which also contains a functional moiety that can be used for attachment. In some instances, other reactive groups of the biomolecule or label are protected to prevent them from reacting with the functional group of the core compound. For example, amino acid side chains containing amino groups, such as arginine, may need to be protected to prevent the side chain from reacting, although in some embodiments the attachment is done via a functional moiety of an amino acid side chain. Protecting groups and techniques are well known in the art. Once the core compound and the biomolecule or label are made, they can be attached by reacting the functional groups. In some instances, the linkage is direct; for example a compound containing a carboxy R group may be directly linked to an amino terminus of a polypeptide. C-terminal attachment may be done using a compound with a amino functional moiety. As is known in the art, this direct linkage may be done in organic solvents or alternatively using coupling reagents such as 1-(3-dimethylaminopropyl)-3-ethylcarbodiimide (EDC) (see generally, March, *Advanced Organic Chemistry*, 3rd Ed, Kiley & Sons, Inc. (1985); see also the 1994 Pierce Chemical Company catalog, technical section on cross-linkers, pages 155–200, incorporated herein by reference).

In a preferred embodiment, the linkage between the two functional moieties may utilize a linker, also well known in the art. For example, two amino groups may be linked via a stable bifunctional groups as are well known in the art, including homobifunctional and heterobifunctional linkers (see Pierce Catalog and Handbook, pages 155–200). In an additional embodiment, carboxy groups (either from the biomolecule or linker or the core compound) may be derivatized using well known linkers (see the Pierce catalog). For example, carbodiimides activate carboxy groups for attack by good nucleophiles such as amines (see Torchilin et al., Critical Rev. Therapeutic Drug Carrier Systems, 7(4) :275–308 (1991), expressly incorporated herein). Sulfhydryl groups may be added to amines or carboxy groups with heterobifunctional linkers (see the Pierce catalog).

For example, as is known in the art for attachment at the $R_1$ position, nucleic acids may be attached via the deoxy- or ribophosphate backbone, either via hydroxy groups on the carbohydrate or via the phosphate group (see Pirrung et al., (1995), supra; Pillai et al., supra; and Pirrung, 1994, supra; hereby expressly incorporated by reference). Alternatively, the phosphodiester linkage between two nucleotides may be altered to form phosphoramide, phosphorothioate, phosphorodithioate, or O-methylphosphoroamidite linkages, as is known in the art. The nitrogen or sulfur atoms are then used as functional moieties. The nucleotide dimer, containing the altered linkage, may be added to the nucleotide at any position. Then the nucleic acid containing the functional group may be added to the compound either directly or via a linker, as is outlined below for polypeptides.

Functional groups on the nucleotide bases themselves may also be used, such as the amino groups on adenosine and cytosine, or modified bases such as is known for thymine (see for example Telser et al., J. Amer. Chem. Soc. 111:7221–7226 (1991); Unglisch et al., Angew. Chem 103:629–646 (1991); Angew. Chem. Int. Ed. Engl. 30:613–629 (1991); Goodchild, Bioconjugate Chem. 1:165–187 (1990); and Brun et al., J. Amer. Chem. Soc. 113:8153–8159 (1991)). This may be desirable in situations where the nucleic acid is to be caged, i.e. inactivated until photolysis. Thus for example, it may be desirable to prevent the nucleic acid from hybridizing to a target sequence until after photolysis, in which case it may be desirable to cage the nucleic acid at one of its bases to prevent hybridization.

When a polypeptide is to be added at any of the R positions, a variety of linkages may be used. The polypeptide may be attached using either the amino functionality at the N-terminus or the carboxy functionality at the C-terminus. Alternatively, an amino group of an amino acid side chain may be used, such as the amine groups of arginine, asparagine, glutamine, lysine, histidine and tryptophan. Similarly, the linkage may be accomplished using the sulfur atoms of the side chains of methionine or cysteine. The carboxy groups of the side chains of glutamic acid and aspartic acid may also be used.

Similarly, other biomolecules such as carbohydrates, lipids, and hormone targeting moieties may be altered to contain functional groups for linkages, as will be appreciated in the art, or derivatized with linkers containing functional groups. Generally, these biomolecules containing suitable functional groups are made using well known techniques.

When the compounds of the invention are to be used to cage one or two molecules, the site of attachment of the caged molecule is chosen to decrease or eliminate the biological activity of the caged molecule until after photolysis. The molecule to be caged may be attached at either the $R_1$ site or at one of the other R positions. The advantage of attachment at the $R_1$ position is that the molecule attached at the $R_1$ position does not contain the phenylbenzylfuran photolysis product after photolysis. Additionally, two molecules may be caged by attachment of one at the $R_1$ position and the other at a different R site. As discussed above, in some cases the functional group for coupling is chosen to decrease or eliminate the biological function of the biomolecule while the biomolecule is attached to the compound. In other cases, this is not necessary.

Once synthesized, the compounds of the invention find use in a number of applications.

The compounds of the invention can be used as protecting groups for organic synthesis, as is known in the art for benzoins. For example, photochemically-removable protecting groups are useful in organic synthesis, semiconductor lithography, cell biology, X-ray crystallography, solid-based and polymer-based chemistries, and phosphoramidite-based DNA synthesis for light-directed spatially-addressable parallel synthesis for the preparation of surface-bound arrays of DNA probes (see Pirrung et al., J. Org. Chem. 60:1116–1117 (1995); Pirrung et al., Tetrahedron Letters 36(33) :5883–5884 (1995); Pirrung et al., J. Org. Chem. 59:3890–3897 (1994); Cameron et al., J. Chem. Soc. Chem. Commun. 1995, p923–924; McCray et al., Annu. Fev. Biophys. Biophys. Chem. 18:239–270 (1989); Sheehan et al., supra; Gurney et al., Physiological Rev. 67(2):583 (1987); Baldwin et al., Tetrahedron 46(19):6879–6884 (1990); Corrie et al., supra; Mendel et al., J. Am. Chem. Soc. 113:2758–2760 (1991); Pillai, supra; and references cited therein, hereby incorporated by reference).

The compounds of the invention are also useful in the synthesis of caged compounds. One difficulty in the synthesis of caged compounds has been premature photolysis. In the described synthesis, this problem is circumvented by dithiane protection of the benzoyl carbonyl. Photolysis of the linker is therefore prevented, until the dithiane "safety-catch" is removed. Since dithianes may be removed under a variety of mild conditions, many substrates may be caged and manipulated with no special precautions against photolysis, until the dithiane is removed. This safety-catch offers a significant advantage over other currently available cage compounds and photolabile protecting groups.

This type of caging has been done with caged ATP for studies of muscle fiber contraction, where diffusion of ATP into the muscle fiber is slow (Goldman et al., Nature 300:701 (1982)); with caged fluorescent probes that only emit light after photolysis (Cummings et al., Tet. Lett. 29:65 (1988)); and with caged enzymes by incorporating photolabile groups on essential side chains (Mendel et al., J. Am. Chem. Soc. 11 3:2758 (1991)). This caging mechanism also finds use in protein folding studies. For example, as shown in the Examples, a linker of the invention was incorporated within the backbone of a decapeptide. This system is useful for studies of protein conformation and folding, in that the amino acid composition of a target peptide can be drastically altered with a photolysis pulse. In order to facilitate the peptide synthesis, the benzylic hydroxyl of the linker (compound 4 in FIG. 3) was protected as the Fmoc-ester (compound 10 in FIG. 3). This protected linker may be included in any synthetic sequence by standard Fmoc solid-phase synthesis protocols (see Bodanszky et al., *The Prac-* tice of *Peptide Synthesis*, 2nd. Ed.; Springer-Verlag: New York, 1994)). In this embodiment, the dithiane can be removed with a solution of bis(trifluoroacetoxy) iodobenzene (see Fields et al, Int. J. Peptide Protein Res. 35:161 (1990)) prior to TFA cleavage of the peptide, in order to avoid acidolysis of the linker. The peptide can be photolyzed to yield three products: the N-terminal peptide, and two C-terminal peptides corresponding to the two isomeric forms of the phenylbenzofuran photoproduct (FIG. 3).

The compounds of the invention can also be used as photolabile linkers. Many of the properties of the substituted benzoin described above combine to make it an ideal photolabile linker for a variety of applications. Photolysis is extremely rapid, producing a high yield of isolated photoproducts. The linker may be photolyzed by 308–366 nm light, which allows photolysis to proceed without competing absorption by organic moieties that absorb further to the blue. On the other hand, the linker itself, in general, is sufficiently transparent from 308–366 nm to prevent inner filter effects from interfering with the course of the photolysis. The phenylbenzofuran photoproducts are expected to be inert (Pirrung, supra, 1994), and their production may be easily monitored generally at 310 nm. Finally, the linker is generally photochemically inert until removal of the dithiane. Combined, these attributes make the compounds of the invention, such as as depicted in Formulas 1 and 2, a valuable photolabile linker.

In a preferred embodiment, the compounds of the invention are used as novel fluorescent probes. Cellular traffic and the effects of cellular stimuli on cellular traffic are areas of active research. The goal is to understand how extra-and intra-cellular signals affect the trafficking and accumulation of important biomolecules. The most common method of studying cellular traffic is through the use of fluorescent probes which can be covalently linked to biomolecules and thus allow for easy identification and quantitation. These cellular trafficking studies are hampered, in part, by the inability to generate a specific fluorescent signal at a particular site in a cell. Consequently if a fluorescent-labeled biomolecule is introduced into a cell, it distributes throughout its targeted organelles and fluorescence measurements can be performed to determine the location and quantity of such biomolecules. If the cell environment is then perturbed, only gross changes in the labeled biomolecule concentration and location can be detected. As a result, it is possible to observe a large increase in fluorescence in one organelle and a decrease in another in such an experiment, but information about the pathway of transport, where small populations of the biomolecule may be present, is lost. This is due to the fact that only intensity differences at the emission wavelength of the fluorophore can be observed using such techniques. For the same reason, it is impossible to study steady-state transport processes by these standard fluorescence techniques.

This situation could be remedied if a second, independent fluorescent signal could be introduced on the biomolecule at a specific site in the cell and at a specific time that corresponds to the perturbation event. Furthermore, it would be useful if the resultant independent fluorescent signal was widely separated in wavelength from the initial fluorescent signal. In short, a fluorescent probe that can rapidly change emission colors in response to a photolysis pulse would be quite desirable. For example, using such a probe it would be possible to flash a small region of a red labeled biomolecule, converting it to blue. If the photolysis pulse coincides with a perturbation of the cell environment, it would be possible to track the movement of the now blue biomolecule against the red background directly. Other methods which convert a nonfluoresent molecule to a fluorescent one are expected to be less effective than the present methods since they do not allow for direct imaging of the biomolecule initially and show extremely poor quantum yields (Cummings et al., Tetrahedron Letters 29, 1, 65, and references therein).

Thus, the compounds of the invention find use as novel fluorescent probes.

The invention utilizes photoactivatable groups based upon 3',5'-dimethoxybenzoin that allows for the direct coupling of a biomolecule of interest to a fluorescent label. Upon photoactivation this linkage is converted to a highly fluorescent benzofuran adduct and in the process releases the fluorescent label, thus converting the biomolecular tag from one fluorophore to another. In such a manner small concentrations of biomolecules can be monitored from the time of photoactivation.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Synthesis of Dithiane Adducts

As outlined above, substituted methoxybenzoins have remarkable photocleavage properties, yet must be keep in complete darkness to prevent premature photolysis. Herein we describe the effective implementation of the Corey-Seebach dithiane addition for the synthesis of benzoins via the dithiane protected adduct 2. As examples, we targeted several benzoins whose synthesis has been reported to give poor or no yield via traditional methods. We further report that the dithiane adduct 2a serves as a very convenient synthon for the introduction of the 3',5'DMB photocleavable protecting group. In such a manner, complex protected molecules can be synthesized that remain photochemically stable until the desired conversion of the dithiane moiety to the parent ketone is accomplished. As an example, we synthesized O-acetyl-3'-carbamylmethoxybenzoin (1e) in 6 steps, (scheme 2) from starting 3-hydroxy benzaldehyde, via the intermediate 3'-TBDMSO-dithiane protected benzoin (2e) with an overall isolated yield of 60%.

In pursuing the synthesis of 3',5'DMB a number of synthetic methods (A-I of Table, below were attempted. These methods, while effective, gave poor to moderate yields of the desired benzoin, (Table 1), and were deemed inefficient for our purposes. The final method involved the addition of the 2-phenyl-1,3-dithiane lithium anion (PDLA) to 3,5-dimethoxybenzaldehyde in THF according to the procedures described by Corey and Seebach, supra (Method 1). Previous investigators had reported that a similar method gave poor yields of the desired benzoin (U.S. Pat. No. 4,469,774). In our hands, however, the PDLA readily reacted with the aldehyde to give a quantitative yield of the dithiane adduct 2. Subsequent deprotection using a variety of standard methods (see Greene, supra) smoothly converted the dithiane adduct to the desired benzoin in near quantitative yields. To demonstrate the utility of this method we have synthesized benzoins 1b–1e via the dithiane adduct in excellent yields (Table 1).

TABLE 1

| Benzoin | Method | % Yield Dithiane[1] | % Yield Benzoin | Lit % Yield[2] |
|---|---|---|---|---|
| 3',5'-dimethoxy (1a) | A–H (see text) | — | 0–55 | 0–61 |
| same | I (see text; this work) | >99 | 96 | — |
| 4'-methoxy (1b) | A | — | — | 50–74 |
| same | I | 97 | 99 | — |
| 2'-ethoxy (1c) | A | — | — | 14 |
| same | I | >99 | 97 | — |
| 2'-methyl (1d) | A | — | — | 15 |
| same | I | >99 | 95 | — |
| 3'-TBDMSO (1e) | I | 93 | 98[3] | — |

[1] determined from GC/MS analysis using an HP4100 GCMS equipped with a 10 meter silicon gum column
[2] from Sheehan et al., J. Am. Chem. Soc. 1971 93:7222; Baldwin et al., Tetrahedron 46:6879 (1990); Corrie et al., J. Chem. Soc. Perkin. Trans. 1:2409 (1992); Pirrung et al., J. Org. Chem. 59:3890 (1994); Harrison et al., Compendium of Organic Synthetic Methods, vol II. John Wiley and Sons, Inc. New York, 1974, pp302–307; Hegedus et al., Compendium of Organic Synthetic Methods, Vol. III, John Wiley and Sons, New York, 1977, pp366–369; Wade et al., Compendium of Organic Synthetic Methods, Vol. II, John Wiley and Sons, New York, 1980, pp375–379.
[3] Yield determined for the O-acetyl-3'-carbamylmethoxybenzoin, see text.

Method A: A standard benzoin condensation between 3,5-dimethoxybenzaldehyde and benzaldehyde was unsuccessful in accord with previously reported results (see Harrison et al., supra, Hegedus et al., supra, and Wade et al.

Method B: Benzoin condensation using phenylmagnesium bromide and the cyanohydrin of the desired aldehyde, yields 12–27%.

Method C: Synthesis via the corresponding 3',5'-dimethoxydesoxybenzoin was also attempted using a variety of methods. Oxidation with iodosobenzoic acid and hydrolysis of the corresponding epoxide afforded a mixture of diasteromers in 30–50% yield.

Method D: 3',5'-dimethoxydesoxybenzoin was treated with one equivalent of $I_2$ in the presence of light, TMSCl, AcOH, or DMAP gave no reaction.

Method E: 3',5'-dimethoxydesoxybenzoin was treated with I equivalent of $Br_2$ in DCM, a quantitative yield of the ring brominated product was formed.

Method F: 3',5'-dimethoxydesoxybenzoin was treated with 1.1 equivalents of thionyl chloride at room temperature in $CCl_4$. A high yield of the ring halogenated product was isolated.

Method G: Similar to the method of Krepski et al., Tetrahedron Letters 24, 38:4075 (1983), except that the O-TMS cyanohydrin of 3', 5'-dimethoxybenzaldehyde was generated by treatment of the benzaldehyde with 1.1 equivalents of KCN and TMSCl in $CH_3CN$ at room temperature, yields of 34–40%.

Method H: Procedure was identical to that described by Krepski et al., supra, with yields 42–55%.

Method 1: A solution of 2-phenyl-1,3-dithiane (390 mg, 2 mM) in 20 mL of dry THF was cooled to 0C and 1.01 equivalents of nBuLi was added dropwise via syringe with rapid stirring. This solution was allowed to stir for 30 minutes and then 1.0 equivalents of the desired benzaldehyde, dissolved in 1 ml dry THF was added dropwise. The solution was allowed to warm to room temperature and stir for 1 hr. The reaction was quenched by the addition of aqueous $NH_4Cl$. THF solvent is removed in vacuo and the resultant slurry extracted with dichloromethane. The DCM was washed with 2 X 20 mL of water and solvent removed in vacuo to yield a pale yellow oil. The obtained oils typically crystallize upon standing and are greater than 99% pure based on GC/MS. $H^1$ NMR and TLC. As such, they can be used for further synthetic transformations without purification.

Example 2

Synthesis of a Photolabile Linker

The linker described below is based on the 3'-methoxybenzoin protecting group described by Sheehan et al. supra. Carboxylic and phosphate esters of appropriately substituted benzoins cleanly and rapidly photolyze in high yields when exposed to light between 308 nm and 366 nm. A suitable linker may be derived from this compound by incorporation of a carboxylic acid moiety, (or other moieties as is generally described herein). Thus, in compound 4, depicted in FIG. 1, a carboxy group was added to the 3'-methoxy substituent, to provide the second functional group for linkage. The benzoyl ring was left unsubstituted.

General: THF was refluxed over sodium and benzophenone, and was distilled prior to use. 3-hydroxybenzaldehyde (Fluka) was dissolved in diethyl ether, filtered through a plug of neutral alumina, and evaporated. All other starting materials were from Aldrich and used without further purification. The 1.0M tetrabutylammonium fluoride (TBAF) solution in THF was dried over 3A molecular seives. IR spectra were acquired from a thin film of the sample on a polyethylene substrate.

Synthesis of 3-(tert-butyldimethylsilyloxy)benzaldehyde (1): The hydroxyl of 3-hydroxybenzaldehyde was protected as the TBDMS ether, to circumbent dianion solubility problems. To a solution of 3-hydroxybenzaldehyde (12.21 g, 100 mmol) in 600 mL THF was added tert-butyldimethylsilyl chloride (TBDMSCl, 18.84 g, 125 mmol). The solution was cooled to 0° C. and triethylamine (12.65 g, 17.4 mL, 125 mmol) was added dropwise. The reaction mixture was brought to room temperature and stirred 5 hours. The mixture was filtered and the THF removed under reduced pressure. The oil was repeatedly dissolved in 200 mL portions of THF and evaporated, until no more triethylamine hydrochloride precipitated. The oil was then dissolved in 150 mL diethyl ether, filtered through a plug of neutral alumina and activated charcoal to remove the salt and the yellow color, and evaporated. The colorless, mobile oil was dried in vacuo overnight. Yield: 21.43 g (91%). IR: 1703, 1583, 1482, 1278, 1145, 840cm$^{-1}$. $^1$H NMR (CDCl$_3$, TMS) d 9.927 (s, 1 H), 7.447 (d, J=7.50 Hz, 1 H), 7.379–7.335 (m, 2 H), 7.096–7.074 (m, 1 H), 0.994 (s, 9 H), 0.215 (s, 6 H). $^{13}$C NMR (CDCl$_3$, TMS) d 191.60, 156.34, 138.03, 130.03, 126.34, 123.46, 119.70, 25.59, 18.12, –4.52. Anal. Calcd for $C_{13}H_{20}O_2Si$: C, 66.05; H, 8.53. Found: C, 66.13; H, 8.53.

Synthesis of (±)-1-hydroxy-1-(3-tert-butyldimethylsilyloxyphenyl)-2-phenyl-2-(1,3-dithian-2-yl)-ethane (2): A solution of 2-phenyl-1,3-dithiane (15.71 g, 80 mmol) in 125 mL THF was prepared. The solution was treated at 0° C. under a nitrogen atmosphere with 40 mL of n-butyllithium (2.0M in cyclohexane, 80 mmol). After 30 min, 1 (18.91 g, 80 mmol) was added. The solution was stirred for 1 hr. at 0° C., then poured into 100 mL of 1N HCl and extracted with methylene chloride (4 X 50 mL). The organic phase was washed with brine, dried with Mg$_2$SO$_4$, filtered through a plug of activated charcoal and silica gel, and evaporated under reduced pressure. The resulting oil was crystallized from ethanol/water to form a white powder. Yield: 28.98 g (84%). mp 75°–76° C. IR: 3449 (br), 1601, 1484, 1275, 1152, 834 cm[1]. $^1$H NMR (CDCl$_3$, TMS) d 7.70 (d, J=7.50 Hz, 2 H), 7.308–7.235 (m, 3 H), 6.937 (t, J=7.79 Hz, 1 H), 6.682–6.660 (m, 1 H), 6.427–6.404 (m, 2 H), 4.926 (d, J=3.73 Hz, 1 H), 2.936 (d, J=3.76 Hz, I H), 2.739–2.610 (m, 4 11), 1.942–1.879 (m, 2 I), 0.935 (s, 9 H), 0.111 (s, 6 H). $^{13}$C NMR (CDCl$_3$, TMS) d 154.43, 138.89, 137.47, 130.42, 128.00, 127.69, 127.36, 121.23, 119.89, 119.54, 80.74, 66.36, 27.22, 26.93, 25.65, 24.69, 18.03, –4.40. Anal. Calcd. C$_{23}$H$_{32}$O$_2$S$_2$Si: C, 63.84; H, 7.45.

Found: C, 63.83; H, 7.26.

Synthesis of (±)-1-hydroxy-1-(3-carbomethoxymethoxyphenyl)-2-phenyl-2-(1,3-dithian-2-yl)-ethane (3): The phenolic hydroxyl was conveniently and selectively alkylated by treatment with TBAF in the presence of methyl bromoacetate, to yield the methyl ester 3. A solution of 2 (28.12 g, 65 mmol) and methyl bromoacetate (12.43 g, 81.25 mmol) in 150 mL dry THF was prepared under a nitrogen atmosphere. The solution was treated with 1M TBAF in THF (68.25 mL, 68.25 mmol) dropwise. The solution was allowed to react overnight, then was poured into ethyl acetate (200 mL) and washed with water (5 X 50 mL). The organic phase was dried with Mg$_2$SO$_4$ and evaporated. The residue was dissolved in 200 mL diethyl ether, filtered through a small quantity of neutral alumina and activated charcoal and dried in vacuo. The product was crystallized from ethyl acetate/hexanes, to afford a white powder. Yield: 23.61 g (93%). mp 122°–122.5° C. IR: 3471 (br), 1760, 1595, 1441, 1211, 714 cm$^{-1}$. $^1$H NMR (CDCl$_3$, TMS) d 7.679 (dd, J=8.16, 1.55 Hz, 2 H), 7.265–7.325 (m, 3 H), 7.045 (t, J=7.92 Hz, 1 H), 6.804–6.782 (m, 1 H), 6.553 (d, J=7.61 Hz, 1 H), 6.302 (s, 1 H), 4.960 (d, J=3.51 Hz, 1 H), 4.367 (s, 2 H), 3.778 (s, 3 H), 3.023 (d, J=3.52 Hz), 2.757–2.620 (m, 4 H), 1.951–1.891 (m, 2 H). $^{13}$C NMR (CDC$_3$, TMS)d 169.17, 156.61, 138.88, 137.40, 130.46, 128.08, 127.98, 127.49, 121.76, 115.35, 113.68, 80.73, 66.32, 52.11, 27.30, 26.99, 24.74. Anal. Calcd. for C$_{10}$H$_{22}$O$_4$S$_2$: C, 61.51; H, 5.68. Found: C, 61.34; H, 5.75.

Synthesis of (±)-1-hydroxy-1-(3-carboxymethoxyphenyl)-2-phenyl-2-(1,3-dithian-2-yl)-ethane (4): A solution of anhydrous lithium iodide (2.68 g, 20 mmol, Aldrich) in 25 mL dry pyridine was brought to reflux under a nitrogen atmosphere and treated with 3 (1.95 g, 5 mmol). The reaction was refluxed for 6 h, then allowed to cool to room temperature under a stream of nitrogen. The solution was poured into 1N HCl (300 mL), and extracted with ethyl acetate (3 X 50 mL). The combined ethyl acetate layers were extracted with 5% sodium bicarbonate (4 X 50 mL). The aqueous phase was acidified to pH 2, and extracted with ethyl acetate (3 X 50 mL). The organic phase was dried with Mg$_2$SO$_4$, filtered through activated charcoal, evaporated, and triturated with hexanes to yield a white solid. Yield: 1.71 g (91%). mp 99°–101° C. IR: 3448 (br), 1735, 1595, 1462, 1232, 719 cm$^{-1}$. $^1$H NMR (CDCl$_3$, TMS) d 7.656 (dd, J=8.00, 1.71 Hz, 2 H), 7.299–7.254 (m, 3 H), 7.036 (t, J=7.98 Hz, 1 H), 6.794–6.773 (m, 1 H), 6.573 (d, J=7.55 Hz, 1 H), 6.251 (s, 1 H), 4.955 (s, 1 H), 4.357 (s, 2 H), 2.728–2.620 (m, 4 H), 1.914–1.868 (m, 2 H). $^{13}$C NMR (CDCl$_3$, TMS) d 173.47, 156.32, 139.01, 137.40, 130.50, 128.12, 128.07, 127.56, 122.02, 115.43, 113.66, 80.56, 66.13, 64.73, 27.26, 26.96, 24.67. Anal. Calcd. for C$_{19}$H$_{20}$O$_4$S$_2$: C, 60.62; H, 5.35. Found: C, 60.36; H, 5.21.

Synthesis of (±)-1-hydroxy-1-(3-carbamylmethoxyphenyl)-2-phenyl-2-(1,3-dithian-2-yl)-ethane (5): A solution of 4 (391 mg, 1 mmol) was prepared in 50 mL methanol with gentle warming. The solution was cooled to 0° C., and gaseous ammonia was bubbled through for 30 min. The flask was wrapped in a towel, securely stoppered, and allowed to come to room temperature. After 2 h, the solvent was removed under reduced pressure to yield a white solid. Yield: 348 mg (93%). mp 140°–141° C. IR: 3460, 3346 (br), 1680, 1586, 1442, 1252, 1058.714cm$^{-1}$. $^1$H NMR (CDCl$_3$, TMS) d 7.686 (dd, J=7.82, 1.70 Hz, 2 H), 7.336–7.291 (m, 3 H), 7.088 (t, J=7.93 Hz, 1 H), 6.774 (dd, J=8.09, 2.55 Hz, 1 H), 6.626 (d, J=7.67 Hz, 1 H), 6.463 (s, br, 1 H), 6.335 (s, 1 H), 5.582 (s, br, 1 H), 4.971 (d, J=3.16 Hz, 1 H), 4.245 (s, 2 H), 3.092 (d J=3.24 Hz, 1 H), 2.777–2.635 (m, 4 H), 1.962–1.905 (m, 2 H). $^{13}$C NMR (CDCl$_{13}$, TMS) d 170.699, 156.059, 139.293, 137.529, 130.437, 128.245, 127.696, 122.261, 114.772, 114.270, 80.706, 67.077, 66.462, 27.342, 27.002, 24.729. Anal. Calcd. for C$_{19}$H$_{21}$NO$_3$S$_2$: C, 60.77; H, 5.64; N, 3.73. Found: C, 60.93; H, 5.79; N, 3.76.

Synthesis of (±)-1-acetoxy-1-(3-carbamylmethoxyphenyl)-2-phenyl-2-(1,3-dithian-2-yl)-ethane (6): To a solution of 5 (192 mg, 0.5 mmol) in 10 mL THF was added DMAP (2 mg), triethylamine (70 mL, 0.5 mmol), and acetic anhydride (94 mL, 1.0 mmol). The solution was stirred at room temperature for 4 h, and then partitioned between ethyl acetate (50 mL) and 5% sodium bicarbonate (50 mL). The organic phase was washed with water (3 X 5 50 mL), dried with Mg$_2$SO$_4$, and evaporated to yield a colorless oil. Yield 205 mg (98%). IR: 3479, 3331 (br), 1747, 1694, 1589, 1 443, 1224, 1033, 910, 718 cm$^{-1}$. $^1$H NMR (CDCl$_3$, TMS) d 7.740 (dd, J=8.15, 1.55 Hz, 2 H), 7.348–7.281 (m, 3 H), 7.111 (t, J=7.96 Hz, 1 H), 6.801 (dd, J=8.18, 2.53 Hz, 1 H), 6.686 (d,J=7.59 Hz, 1 H), 6.521 (s, 2 H), 6.312 (s, 1 H), 6.136 (s, 1 H), 4.238 (s, 2 H), 2.751–2.597 (m, 4 H), 2.104 (s, 3 H), 1.933–1.857 (s, 1 H). $^{13}$C NMR (CDCl$_3$, TMS) d 171.080, 169.318, 156.012, 136.974, 130.771, 128.402, 128.045, 127.738, 122.586, 115.072, 114.635, 79.890, 66.982, 63.133, 27.270, 27.109, 24.568, 20.848. Anal. Calcd. for C$_{21}$H$_{23}$NO$_4$S$_2$: C, 60.41; 11, 5.55; N, 3.5. Found: C, 5 9.92; H, 5.76; N, 3.14.

Synthesis of (±)-O-acetyl-3'-carbamylmethoxybenzoin (7): To a solution of 6 (110 mg, 0.26 mmol) in 5 mL 9:1 (v/v) acetonitrile/water was added mercuric perchlorate (148 mg, 0.33 mmol). The solution was stirred for 15 min, filtered through a 0.45 mm PTFE syringe filter (Gelman) into a 5% sodium bicarbonate solution (10 mL), and extracted with 50 ml methylene chloride. The organic phase was dried and evaporated under reduced pressure to yield a colorless oil. Samples for analysis were evaporated from methanol, dissolved in warm water and lyophilized. Yield: 65 mg (76%). IR: 3445, 1743, 1694, 1462, 1236, 1075, 720 cm$^{-1}$. $^1$H NMR (CDCl$_3$, TMS) d 7.936 (d, J=7.82 Hz, 2 H), 7.529 (t,J=7.56 Hz, 1 H), 7.412 (t, J=7.57 Hz, 2 H), 7.319 (t, J=7.86Hz, 1 H), 7. 139(d, J=7.51 Hz, 1 H), 7.051 (s, 1 H), 6.884 (dd, J=8.21, 2.75 Hz, 1 H) 6.835 (s, 1 H), 6.558 (s, 1 H), 6.148 (s, 1 H), 4.462 (s, 2 H), 2.207 (s, 3 H). $^{13}$C NMR(CDCl$_3$,TMS)d 193.577, 170.825, 170.348, 157.593, 135.473, 134.494, 133.637, 130.516, 128.768, 128.711, 122.371, 115.205, 115.140, 77.144, 67.115, 20.715. Anal. Calcd. for C$_{18}$H$_{17}$NO$_5$H$_2$O: C, 62.59; H, 5.54; N, 4.05. Found: C, 62.53; H, 5.12; N, 3.90.

Steady-state photolysis of 7: A 47.7 mM solution of 7 in 1:1 methanol/Tris.HCl (0.05M, pH 7.40) was prepared in a 1 cm pathlength quartz cuvette. The sample was irradiated by an Oriel 66011 Hg vapor lamp operating at 450 watts, filtered with a water cooled Schott glass UG11 filter. At intervals, the sample was removed, and the UV absorption spectrum from 210–400 nm taken by a HP 8452 spectrophotometer. Complete photolysis occurred within a 90 sec exposure.

For isolation of the photoproduct, a 25.6 mg sample of 7 in 50 mL methanol was irradiated in 3 mL batches as above, until no further change was observed in the absorption spectrum of the sample. The methanol was removed under reduced pressure to yield 20.6 mg (99%) of the photoproduct. The composition of this material was 74% 2-phenyl-5-carbamylmethoxy-benzofuran (8), 24% 2-phenyl-7-carbamylmethoxy-benzofuran (9), and 2% other material, as determined by GCMS. Standard samples were obtained by preparative-TLC (silica gel/diethyl ether) of the crude photolyzed sample, and identified by $^1$H NMR and IR.

Transient photolysis of 7: A 9.54 mM solution of 7 in 1:1 methanol/Tris-HCl (0.05M, pH7.40) was prepared in a 1 cm pathlength quartz cuvette. The sample was photolyzed using the third harmonic at 355 nm from a Q-switched Spectra Physics DCR-12 Nd:YAG laser. Typical pulses were 10–20 ns (FWHM) in duration at an energy of 1.5 mJ/pulse. The sample was monitored with a 75 W xenon arc lamp filtered with a Schott glass UG11 filter placed between the arc lamp and the cuvette. The probe light exiting the cuvette was then wavelength selected by a SA 1690B double monochromator set at 310 nm, and was detected with a photomultiplier. The signal was amplified with a Keithly 427 current amplifier, and digitized by a Tektronix $R_7$10 200 MHz transient digitizer interfaced to a microcomputer. Samples were acquired at a 10 Hz photolysis pulse repetition rate, and scans represented the average of 20 pulses.

Irradiation of 7 resulted in a clean conversion to the phenylbenzofurans 8 and 9. Steady-state photolysis spectra of 7 show two isosbestic points throughout the course of the photolysis (FIG. 3). The two isomeric photoproducts 8 and 9 were produced in a 98% yield at a ratio of 3:1 as determined by GCMS and NMR of the isolated phenylbenzofurans, along with an equivalent of acetic acid.

Due to the large absorption change at 310 nm ($\Delta\epsilon=35,000M^{-1} cm^{-1}$), transient absorption studies of the formation of 8 and 9 were performed. Quenching studies by Sheehan et al. supra, showed that photolysis of 3',5'-dimethoxybenzoin acetate is extremely rapid, with a rate on the order of $10^{10}$ sec$^{-1}$. Rapid photolysis seems to have been preserved in the benzoin acetate 7. Photolysis of 7 with a frequency tripled Nd:YAG laser at 355 nm resulted in a rapid absorption increase at 310 nm. The course of this increase could not be measured within the instrument response time of approximately 30 ns, which places a lower limit on the photolysis rate of 3 X $10^7$ sec$^{-1}$ (data not shown).

Example 3

Photolabile Linker Attached to a Polypeptide Biomolecule

As a demonstration of a potential application for this compound, the linker was incorporated within the backbone of a decapeptide. Such a system would be useful for studies of protein conformation and folding, in that the amino acid composition of a target peptide could be drastically altered with a photolysis pulse. In order to facilitate the peptide synthesis, the benzylic hydroxyl of the linker 4 was protected as the Fmoc-ester 10. This protected linker may be included in any synthetic sequence by standard Fmoc solid-phase synthesis protocols.[13] The dithiane was removed with a solution of bis(trifluoroacetoxy)iodobenzene prior to TFA cleavage of the peptide, in order to avoid acidolysis of the linker. This peptide was then photolyzed to yield three products: the N-terminal peptide, and two C-terminal peptides corresponding to the two isomeric forms of the phenylbenzofuran photoproduct (FIG. 2).

Synthesis of (±)-1-fluorenylmethoxycarbonyloxy-1-(3-carboxy methoxyphenyl)-2-phenyl-2-(1,3-dithian-2-yl)-ethane (10): A solution of 4 (1.57 g, 4.17 mmol) in 50 mL THF was prepared under a nitrogen atmosphere. The solution was cooled to −78° C., and n-butyllithium (2.0M in cyclohexane, Aldrich) was added until the dianion precipitates and a persistent yellow color remains [approx. 4 mL, 8 mmol]. The suspension was treated with 9-fluorenylmethyl-succinimidyl carbonate (3.18 g, 9.43 mmol, Bachem) and the cold bath was removed. After 1 hr., the suspension was poured into 1N HCl and extracted with ethyl acetate. The organic phase was dried and evaporated under reduced pressure. The resulting oil was purified by reversed-phase HPLC (C18, 70% to 90% acetonitrile in water, 0.1% TFA, 40 min.). Yield: 1.06 g (42%). IR: 1747, 1597, 1462, 1256, 730 cm$^{-1}$. $^1$H NMR (CDCl$_3$, TMS) d 7.778 (d, J=6.85 Hz, 2 H), 7.739 (dd, J=7.40, 2.47 Hz, 2 H), 7.590 (dd, J=12.18, 7.47 Hz, 2 H) 7.404–7.237 (m, 7 H), 7.115 (t, J=7.94 Hz, 1 H), 6.842 (dd, J=8.24, 2.38 Hz, 1 H), 6.710 (d, J=7.64 Hz, 1 H), 6.346 (s, 1 H), 6.024 (s, 1 H), 4.430–4.393 (m, 3 H), 4.298–4.256 (m, 2 H), 2.778–2.603 (m, 4 H), 1.984–1.856 (m, 2 H). $^{13}$C NMR (CDCl$_3$, TMS) d 173.41, 156.42, 154.02, 143.32, 143.25, 141.25, 141.24, 136.79, 136.17, 130.78, 128.44, 128.13, 127.13, 125.26, 122.51, 119.98, 115.92, 114.17, 83.94, 70.19, 64.77, 62.93, 46.66, 27.26, 27.18, 24.48.

Synthesis of a photolabile peptide: The sequence Ac-Val-Gly-Glu-Arg-Gly-linker-Gly-Arg-Nle-Lys-Glu-NH$_2$ was prepared on an Fmoc-amide resin (Applied Biosystems, Inc.) on a 0.1 mmol scale. Couplings were performed with 10 eq. each of DCC, HOBt, and Fmoc-AA or 10 in NMP for 1 hr. with the exception of Gly-5 which was coupled to the benzylic hydroxyl of the linker with 10 eq. DCC and 0.1 eq DMAP for 24 hrs. The Fmoc groups were removed by 3 X 3 min treatments with 30% piperidine in NMP. The N terminal valine was capped with 10 eq. acetic anhydride and 0.1 eq. DMAP, and the dithiane was removed by treatment with 5 eq. bis(trifluoroacetoxy)-iodobenzene in 9:1 acetonitrile:water for 10 min. The resin was dried and cleaved with 1.8 mL TFA, 0.1 mL water, and 100 mg phenol for 90 min. The crude peptide was isolated by precipitation in methyl butyl ether and purified by RP-HPLC (C 18, water/acetonitrile gradient containing 0.1% TFA).

Steady-state peptide photolysis: The purified peptide HPLC fractions were diluted 10:1 with 25 mM sodium acetate buffer, pH 5.5, and irradiated as for the photolysis of 7. Aliquots were periodically analyzed by RP-HPLC. Maximum photolysis occured after 5 min.

Example 4

Synthesis of a Photoinitiated Fluorescent Probe

Caged compounds based on esters of 3',5'-dimethoxybenzoin are an ideal starting point for a color changing fluorescent probe. This substituted benzoin exhibits subnanosecond photolysis when irradiated from 300–360 nm, and in a high quantum yield of 0.64. The benzofuran photoproduct is highly fluorescent, with an emission maximum at 400 nm. This cage compound can be coupled to a longer wavelength fluorescent probe, such as carboxyfluorescein. The carboxyfluorescein can be excited to fluoresce at wavelengths that do not lead to photolysis, but when a photolysis pulse is applied, the carboxyfluorescein is released, yielding a blue fluorescent photoproduct, as generally depicted in FIG. 4. In order to attach the benzofuran to a biomolecule, one of the methoxy groups is replaced by a carboxymethoxy group, allowing attachment to a variety of functional groups. Alternatively, functionally active moieties other than carboxy may be used.

The photolabile linker 3'-carboxymethoxybenzoin, which has similar photolysis properties to 3',5'-dimethoxy benzoin, and which also has a fluorescent photoproduct, can be synthesized in high yields on the 10 g scale as described above. Briefly, the hydroxyl of 3-hydroxybenzaldehyde is protected as the TBDMS ether, and the aldehyde is condensed with I equivalent of phenyldithiane lithium anion, followed by aqueous workup, as outlined in Example 2. This material, a benzoin with the carbonyl protected as the dithiane, is then alkylated at the 3' position by addition of methyl bromoacetate and tetrabutylammonium fluoride.

Once the carboxymethoxy compound is made, attachment of the desired fluorophore can be accomplished via a number of different methods. Direct acylation of the benzylic hydroxyl with an activated long wavelength fluorophore has been accomplished in the case of carboxyfluorescein. The 3'-methoxy can then be removed by lithium iodide in refluxing pyridine and converted to a hydroxysuccinimide ester. The dithiane is then hydrolyzed by standard procedures to give a photoactive fluorescent compound which can be directly attached to a biomolecule via the succinimide group.

We claim:

1. A compound having the formula

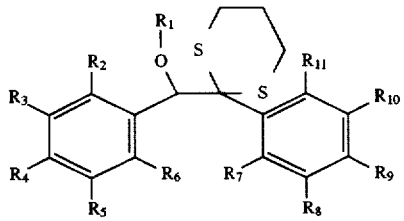

wherein $R_1$ is hydrogen, carboxy, substituted carbonyl, a phosphorus containing group, a sulfur containing group, a fluorescent label or a biomolecule;

$R_2$ is hydrogen, alkyl, aryl, alkoxy or substituted alkoxy;

$R_3$ is hydrogen, alkyl, aryl, alkoxy or substituted alkoxy;

$R_4$ is hydrogen, alkyl, aryl, alkoxy or substituted alkoxy;

$R_5$ is hydrogen, alkyl, aryl, alkoxy or substituted alkoxy;

$R_6$ is hydrogen, alkyl, aryl, alkoxy or substituted alkoxy;

$R_7$ is hydrogen, alkyl, aryl, alkoxy or substituted alkoxy;

$R_8$ is hydrogen, alkyl, aryl, alkoxy or substituted alkoxy;

$R_9$ is hydrogen, alkyl, aryl, alkoxy or substituted alkoxy;

$R_{10}$ is hydrogen, alkyl, aryl, alkoxy or substituted alkoxy;

$R_{11}$ is hydrogen, alkyl, aryl, alkoxy or substituted alkoxy;

wherein at least one of $R_2$ or $R_6$ is hydrogen; and wherein at least one of $R_2$, $R_3$, $R_4$, $R_5$ or $R_6$ is hydroxy or substituted alkoxy.

2. A compound according to claim 1 wherein said substituted alkoxy is substituted with amino, alkyl amino, carboxy, substituted carbonyl, a phosphorus containing group, a sulfur-containing moiety, or a biomolecule.

3. A compound according to claim 1 wherein said $R_1$ group is a fluorescent label.

4. A compound having the formula:

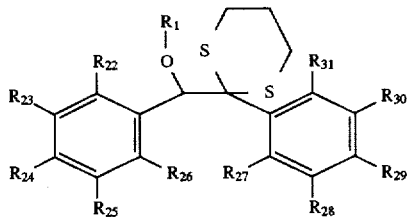

wherein $R_1$ is hydrogen, carboxy, substituted carbonyl, phosphorus-containing moiety, a sulfur containing group, a fluorescent label or a biomolecule;

$R_{22}$ is hydrogen, alkyl, aryl, alkoxy, substituted alkoxy, or a biomolecule;

$R_{23}$ is hydrogen, alkyl, aryl, alkoxy, substituted alkoxy, or a biomolecule;

$R_{24}$ is hydrogen, alkyl, aryl, alkoxy, substituted alkoxy, or a biomolecule;

$R_{25}$ is hydrogen, alkyl, aryl, alkoxy, substituted alkoxy, or a biomolecule;

$R_{26}$ is hydrogen, alkyl, aryl, alkoxy, substituted alkoxy, or a biomolecule;

$R_{27}$ is hydrogen, alkyl, aryl, alkoxy, substituted alkoxy, or a biomolecule;

$R_{28}$ is hydrogen, alkyl, aryl, alkoxy, substituted alkoxy, or a biomolecule;

$R_{29}$ is hydrogen, alkyl, aryl, alkoxy, substituted alkoxy, or a biomolecule;

$R_{30}$ is hydrogen, alkyl, aryl, alkoxy, substituted alkoxy, or a biomolecule;

$R_{31}$ is hydrogen, alkyl, aryl, alkoxy, substituted alkoxy, or a biomolecule;

wherein at least one of $R_{22}$ or $R_{26}$ is hydrogen;

wherein at least one of $R_{22}$, $R_{23}$, $R_{24}$, $R_{25}$ or $R_{26}$ is alkoxy or substituted alkoxy;

and wherein at least one of $R_{22}$, $R_{23}$, $R_{24}$, $R_{25}$ or $R_{26}$ is a biomolecule.

5. A compound according to claim 4 wherein said biomolecule is selected from the group consisting of polypeptides and nucleic acids.

6. A compound having the formula

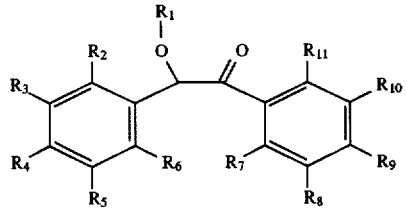

wherein $R_1$ is phosphorus-containing moiety, a sulfur containing group, a fluorescent label or a biomolecule;

$R_2$ is hydrogen, alkyl, aryl, alkoxy or substituted alkoxy;

$R_3$ is hydrogen, alkyl, aryl, alkoxy or substituted alkoxy;

$R_4$ is hydrogen, alkyl, aryl, alkoxy or substituted alkoxy;

$R_5$ is hydrogen, alkyl, aryl, alkoxy or substituted alkoxy;

$R_6$ is hydrogen, alkyl, aryl, alkoxy or substituted alkoxy;

$R_7$ is hydrogen, alkyl, aryl, alkoxy or substituted alkoxy;

$R_8$ is hydrogen, alkyl, aryl, alkoxy or substituted alkoxy;

$R_9$ is hydrogen, alkyl, aryl, alkoxy or substituted alkoxy;

$R_{10}$ is hydrogen, alkyl, aryl, alkoxy or substituted alkoxy;

$R_{11}$ is hydrogen, alkyl, aryl, alkoxy or substituted alkoxy;

wherein at least one of $R_2$ or $R_6$ is hydrogen;

wherein at least one of $R_2$, $R_3$, $R_4$, $R_5$ or $R_6$ is hydroxy or substituted alkoxy.

7. A compound according to claim 6 wherein $R_1$ is a biomolecule.

8. A compound according to claim 6 wherein said substituted alkoxy is substituted with a biomolecule.

9. A compound having the formula

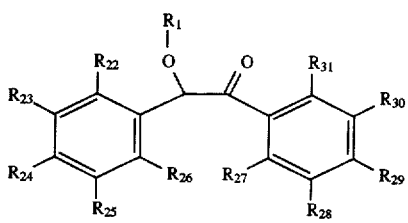

wherein $R_1$ is hydrogen, carboxy, substituted carbonyl, phosphorus-containing moiety, a sulfur containing group, a fluorescent label or a biomolecule;

$R_{22}$ is hydrogen, alkyl, aryl, alkoxy, substituted alkoxy, or a biomolecule;

$R_{23}$ is hydrogen, alkyl, aryl, alkoxy, substituted alkoxy, or a biomolecule;

$R_{24}$ is hydrogen, alkyl, aryl, alkoxy, substituted alkoxy, or a biomolecule;

$R_{25}$ is hydrogen, alkyl, aryl, alkoxy, substituted alkoxy, or a biomolecule;

$R_{26}$ is hydrogen, alkyl, aryl, alkoxy, substituted alkoxy, or a biomolecule;

$R_{27}$ is hydrogen, alkyl, aryl, alkoxy, substituted alkoxy, or a biomolecule;

$R_{28}$ is hydrogen, alkyl, aryl, alkoxy, substituted alkoxy, or a biomolecule;

$R_{29}$ is hydrogen, alkyl, aryl, alkoxy, substituted alkoxy, or a biomolecule;

$R_{30}$ is hydrogen, alkyl, aryl, alkoxy, substituted alkoxy, or a biomolecule;

$R_{31}$ is hydrogen, alkyl, aryl, alkoxy, substituted alkoxy, or a biomolecule;

wherein at least one of $R_{22}$ or $R_{26}$ is hydrogen;

wherein at least one of $R_{22}$, $R_{23}$, $R_{24}$, $R_{25}$ or $R_{26}$ is alkoxy or substituted alkoxy;

and wherein at least one of $R_{22}$, $R_{23}$, $R_{24}$, $R_{25}$ or $R_{26}$ is a biomolecule.

10. A furan obtained by the photolysis of a compound of claim 9.

11. A method for forming the compound of claim 1 or claim 4 comprising contacting

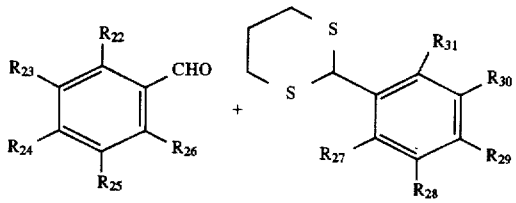

under conditions that allow the reaction of said components to form a dithiane-benzoin adduct;

wherein $R_{22}$ is hydrogen, alkyl, aryl, alkoxy, substituted alkoxy, or a biomolecule;

$R_{23}$ is hydrogen, alkyl, aryl, alkoxy, substituted alkoxy, or a biomolecule;

$R_{24}$ is hydrogen, alkyl, aryl, alkoxy, substituted alkoxy, or a biomolecule;

$R_{25}$ is hydrogen, alkyl, aryl, alkoxy, substituted alkoxy, or a biomolecule;

$R_{26}$ is hydrogen, alkyl, aryl, alkoxy, substituted alkoxy, or a biomolecule;

$R_{27}$ is hydrogen, alkyl, aryl, alkoxy, substituted alkoxy, or a biomolecule;

$R_{28}$ is hydrogen, alkyl, aryl, alkoxy, substituted alkoxy, or a biomolecule;

$R_{29}$ is hydrogen, alkyl, aryl, alkoxy, substituted alkoxy, or a biomolecule;

$R_{30}$ is hydrogen, alkyl, aryl, alkoxy, substituted alkoxy, or a biomolecule;

$R_{31}$ is hydrogen, alkyl, aryl, alkoxy, substituted alkoxy, or a biomolecule;

wherein at least one of $R_{22}$ or $R_{26}$ is hydrogen;

wherein at least one of $R_{22}$, $R_{23}$, $R_{24}$, $R_{25}$ or $R_{26}$ is alkoxy or substituted alkoxy;

and wherein at least one of $R_{22}$, $R_{23}$, $R_{24}$, $R_{25}$ or $R_{26}$ is a biomolecule.

12. A method for forming the compound of claim 1 or claim 4 comprising contacting

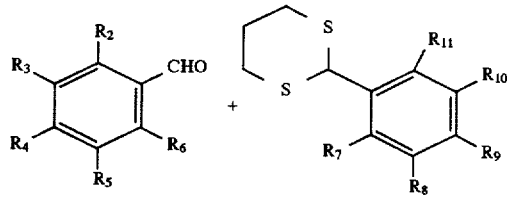

under conditions that allow the reaction of said components to form a dithiane-benzoin adduct;

wherein $R_2$ is hydrogen, alkyl, aryl, alkoxy or substituted alkoxy;

$R_3$ is hydrogen, alkyl, aryl, alkoxy or substituted alkoxy;

$R_4$ is hydrogen, alkyl, aryl, alkoxy or substituted alkoxy;

$R_5$ is hydrogen, alkyl, aryl, alkoxy or substituted alkoxy;

$R_6$ is hydrogen, alkyl, aryl, alkoxy or substituted alkoxy;

$R_7$ is hydrogen, alkyl, aryl, alkoxy or substituted alkoxy;

$R_8$ is hydrogen, alkyl, aryl, alkoxy or substituted alkoxy;

$R_9$ is hydrogen, alkyl, aryl, alkoxy or substituted alkoxy;
$R_{10}$ is hydrogen, alkyl, aryl, alkoxy or substituted alkoxy;
$R_{11}$ is hydrogen, alkyl, aryl, alkoxy or substituted alkoxy;
wherein at least one of $R_2$ or R6 is hydrogen; and
wherein at least one of $R_2$, $R_3$, $R_4$, $R_5$ or $R_6$ is hydroxy or substituted alkoxy.

13. A method of forming the compound of claim 6 or 9 comprising contacting the corresponding dithiane-benzoin adduct of claims 1 or 4 with a reagent capable of removing said dithiane to form the benzoin.

* * * * *

UNITED STATES PATENT AND TRADEMARK OFFICE
CERTIFICATE OF CORRECTION

PATENT NO. : 5,767,288

DATED : June 16, 1998

INVENTOR(S) : Ronald S. Rock, et. Al.

Page 1 of 3

It is certified that error appears in the above-identified patent and that said Letters Patent is hereby corrected as shown below:

In Col. 5, line 6, change "R6" to --$R_6$--.

In Col. 5, line 37, change "R6" to --$R_6$--.

In Col. 5, lines 44 and 45, change "fluoroscent" to --fluorescent--.

In Col. 5, line 63, change "R9" to --$R_9$--.

In Col. 6, line 60, delete "15".

In Col. 7, line 36, change "I" to --1--.

In Col. 7, line 63, change "CH." to --$CH_2$--.

In Col. 9, line 36, change "R6" to --$R_6$--.

In Col. 9, line 64, delete "2 0".

In Col. 17, line 46, change "I" to --1--.

In Col. 17, line 60, change "Method 1" to --Method I--.

UNITED STATES PATENT AND TRADEMARK OFFICE
CERTIFICATE OF CORRECTION

PATENT NO. : 5,767,288

DATED : June 16, 1998

INVENTOR(S) : Ronald S. Rock, et. Al.

It is certified that error appears in the above-identified patent and that said Letters Patent is hereby corrected as shown below:

In Col. 17, line 61, change "OC" to --O° C--.

In Col. 17, line 65, change "I" to --1--.

In Col. 18, line 34, change "3-tert" to --3-*tert*--.

In Col. 18, line 38, change "tert" to --*tert*--.

In Col. 18, line 54, change "(CDCl$_3$" to --(CDCl$_3$--.

In Col. 18, line 57, change "tert" to --*tert*--.

In Col. 18, line 58, change "2-yI" to --2-yl--.

In Col. 19, line 7, change "I H" to --1 H--.

In Col. 19, line 8, change "4 11" to --4 H--; and "2 I" to --2 H--.

In Col 19, line 32, change "Hz.2" to --Hz, 2--.

In Col. 19, line 40, change "$C_{10}$" to --$C_{20}$--.

UNITED STATES PATENT AND TRADEMARK OFFICE
CERTIFICATE OF CORRECTION

PATENT NO. : 5,767,288
DATED : June 16, 1998
INVENTOR(S) : Ronald S. Rock, et. Al.

It is certified that error appears in the above-identified patent and that said Letters Patent is hereby corrected as shown below:

In Col. 19, line 42, change "2-yI" to --2-yl--.

In Col. 20, line 2, change "0°C.," to --0°C,--.

In Col. 20, line 13, change "$CDCl_{13}$" to --$CDCl_3$--.

In Col. 20, line 19, change "2-yI" to --2-yl--.

In Col. 20, line 26, change "(3 x 5 50 mL)" to --3 x 50 mL)--.

In Col. 20, line 28, change "1 443" to --1443--.

In Col. 20, line 37, change "11," to --H,--; and change "5 9.92" to --59.92--.

In Col. 20, line 57, change "$NO_5H_2$" to --$NO_5 \cdot H_2$--.

In Col. 21, line 13, change "Tris-HCl" to --Tris·HCl--.

Signed and Sealed this

Sixteenth Day of February, 1999

Attest:

Attesting Officer

*Acting Commissioner of Patents and Trademarks*

UNITED STATES PATENT AND TRADEMARK OFFICE
CERTIFICATE OF CORRECTION

PATENT NO. : 5,767,288
DATED : June 16, 1998
INVENTOR(S) : ROCK et al.

It is certified that error appears in the above-indentified patent and that said Letters Patent is hereby corrected as shown below:

On the cover page, under Other Publications, third line from the bottom change "[3',5'" to --(3',5')--.

On the cover page, under Other Publications, after "Mendel" insert --Baldwin, J.E., et al., "New Photolabile Phosphate Protecting Groups", Tetrahedron 19:6879-6884 (1990).--.

Signed and Sealed this

Eleventh Day of May, 1999

*Attest:*

Q. TODD DICKINSON

*Attesting Officer*  *Acting Commissioner of Patents and Trademarks*